(12) United States Patent
Lehr et al.

(10) Patent No.: US 7,608,633 B2
(45) Date of Patent: Oct. 27, 2009

(54) HETEROARYL-SUBSTITUTED ACETONE DERIVATIVES AS INHIBITORS OF PHOSPHOLIPASE $A_2$

(75) Inventors: Matthias Lehr, Havixbeck (DE); Joachim Ludwig, Münster (DE)

(73) Assignee: Merckle GmbH, Blaubeuren (DE)

( * ) Notice: Subject to any disclaimer, the term of this patent is extended or adjusted under 35 U.S.C. 154(b) by 615 days.

(21) Appl. No.: 10/544,300

(22) PCT Filed: Feb. 6, 2004

(86) PCT No.: PCT/EP2004/001128

§ 371 (c)(1),
(2), (4) Date: Aug. 4, 2005

(87) PCT Pub. No.: WO2004/069797

PCT Pub. Date: Aug. 19, 2004

(65) Prior Publication Data

US 2006/0142366 A1 Jun. 29, 2006

(30) Foreign Application Priority Data

Feb. 7, 2003 (DE) ................................ 103 05 089

(51) Int. Cl.
| | | |
|---|---|---|
| *A61K 31/4164* | (2006.01) | |
| *A61K 31/415* | (2006.01) | |
| *A61K 31/404* | (2006.01) | |
| *A61K 31/40* | (2006.01) | |
| *C07D 233/61* | (2006.01) | |
| *C07D 231/56* | (2006.01) | |
| *C07D 231/12* | (2006.01) | |
| *C07D 209/12* | (2006.01) | |
| *C07D 207/333* | (2006.01) | |

(52) U.S. Cl. ........................ 514/396; 514/406; 514/419; 514/427; 548/340.1; 548/362.5; 548/376.1; 548/494; 548/562

(58) Field of Classification Search ................ 514/396, 514/406, 419, 427; 548/340.1, 362.5, 376.1, 548/494, 562
See application file for complete search history.

(56) References Cited

U.S. PATENT DOCUMENTS

| | | | |
|---|---|---|---|
| 4,189,594 A | 2/1980 | Grill et al. | .................... 560/53 |
| 5,470,858 A | 11/1995 | Fraire et al. | .............. 514/263.3 |
| 6,924,391 B2 | 8/2005 | Banville et al. | ............. 562/441 |
| 2002/0037875 A1 | 3/2002 | Banville et al. | ................ 514/63 |

FOREIGN PATENT DOCUMENTS

| | | | |
|---|---|---|---|
| DE | 2618979 A1 | * | 11/1976 |
| EP | 0 193 853 | | 9/1986 |
| EP | A-0 520 552 | | 12/1992 |
| GB | 2002763 | | 2/1979 |
| WO | WO 98/05637 | | 2/1998 |
| WO | WO 01/53257 | | 7/2001 |

OTHER PUBLICATIONS

English translation of the International Preliminary Report on Patentability (Chapter I) issued in PCT/EP04/01128 (Sep. 29, 2005).
S. Connolly et al., J. Med. Chem., vol. 45: 1348-1362 (2002).
International Search Report (Form PCT/ISA/210) issued in PCT/EP04/01128.
Written Opinion of the International Search Authority (Form PCT/ISA/237) issued in PCT/EP04/01128 (acknowledging novelty, inventive step and industrial applicability of the invention of claims 1-13).
International Preliminary Report on Patentability issued in PCT/EP04/01128.

\* cited by examiner

*Primary Examiner*—Rei-Tsang Shiao
*Assistant Examiner*—Joseph R Kosack
(74) *Attorney, Agent, or Firm*—Chalin A. Smith; Smith Patent Consulting

(57) ABSTRACT

The invention relates to novel heteroaryl substituted acetone derivatives which inhibit the enzyme phospholipase $A_2$, pharmaceutical preparations containing these compounds and a method of producing these compounds.

18 Claims, No Drawings

HETEROARYL-SUBSTITUTED ACETONE DERIVATIVES AS INHIBITORS OF PHOSPHOLIPASE A$_2$

This application claims priority to German Patent Application No. 103 05 089.2 filed Feb. 7, 2003, the contents of which are incorporated by reference herein in its entirety.

The present invention relates to novel heteroaryl substituted acetone derivatives inhibiting the phospholipase A$_2$ enzyme. These compounds are suited as drugs for preventing and treating diseases caused or contributorily caused by an increased activity of this enzyme, such as inflammations, pain, fever, allergies, asthma, psoriasis and endotoxic shock. The invention also relates to methods of synthesizing these compounds as well as pharmaceutical preparations containing these compounds.

The term "phospholipase A$_2$" comprises the major and diverse group of enzymes which cleave phospholipids at the sn-2 position thereby forming free fatty acids and lysophospholipids. If the released fatty acid is arachidonic acid, the latter can be metabolized into the prostaglandins and thromboxanes via the cyclooxygenase route and into the leukotrienes and other hydroxylated fatty acids via the lipoxygenase route. The prostaglandins are considerably involved in the formation of pain and fever and in inflammatory responses. Leukotrienes are important mediators in the case of inflammatory processes and anaphylactic and allergic processes (Forth et al., *Aligemeine und Spezielle Pharmakologie und Toxikologie*, Spektrum Akademischer Verlag Heidelberg, Berlin, Oxford, 1998).

The lysophospholipids formed by phospholipase A$_2$ have cell-damaging properties. Lysophosphatidylserine releases the histamine involved in allergic processes (Moreno et al., *Agents Actions* 1992, 36, 258). In addition, lysophosphatidylcholine is metabolized into the platelet-activating factor (PAF) which is also an important mediator, e.g. in the case of inflammations.

Various phospholipase A$_2$ forms are known. They comprise Ca$^{2+}$-dependent low-molecular secretory phospholipases A$_2$ (sPLA$_2$), CA$^{2+}$-independent high-molecular phospholipases A$_2$ (iPLA$_2$), CA$^{2+}$-dependent high-molecular cytosolic phospholipases A$_2$ (cPLA$_2$) and Ca$^{2+}$-independent lipoprotein-associated phospholipases A$_2$ (LP-PLA$_2$), formerly also referred to as PAF acetylhydrolase (Six et al., *Biochim. Biophys. Acta.*, 2000, 1488, 1-19). According to the current state of knowledge, the cytosolic phospholipase A$_2$ (cPLA$_2$) plays the key role in the biosynthesis of prostaglandins, leukotrienes, PAFs and lysophospholipids. This was demonstrated inter alia by studies with cPLA$_2$ knock-out mice, i.e. mice no longer having this enzyme (Uozumi et al., *Nature* 1997, 390, 618-622; Bonventre et al., *Nature* 1997, 390, 622-625, Dennis et al., *Journal of Experimental Medicine* 2002, 196, 349-357).

Thus, excess stimulation of this enzyme can result in a number of chronic and acute diseases, such as asthma, cerebral ischemia (Clemens et al., *Stroke* 1996, 27, 527-535), Alzheimer's disease (Stephenson et al., *Neurobiology of Stroke*, 1996, 3, 51-63), rheumatoid arthritis (Huang et al., *Mediators of Inflammation*, 1994, 3, 307-308), chronic skin diseases and damage to the skin caused by U.V. rays (Gresham et al., *American Journal of Physiology* 1996, 270, C1037-C1050).

Inhibitors of cPLA$_2$ can thus be useful for a number of inflammatory diseases.

Inhibitors of cytosolic Phospholipase A$_2$ have already been described in the literature (Lehr, *Drugs of the Future*, 2000, 25, 823-832).

For example, 1,3-disubstituted propan-2-one compounds of AstraZeneca company are known (Connolly et al, *Journal of Medicinal Chemistry*, 2002, 45, 1348-1362). WO 00/34254 discloses compounds having an inhibitory effect on cytosolic phospholipase A$_2$. Patent specifications U.S. Pat. No. 6,414,179, U.S. 2002/0037875 and U.S. 2002/0065246 disclose alpha amino-substituted, thio-substituted and oxo-substituted ketones as well as alpha-substituted and beta-substituted trifluoromethylketones as inhibitors of cytosolic phospholipase A$_2$. Moreover, EP 976 748 discloses certain pyrrolidine derivatives as inhibitors of cytosolic Phospholipase A$_2$.

However, there is still a need for novel compounds which inhibit phospholipase A$_2$ and in particular cytosolic phospholipase A$_2$. It has now been found surprisingly that certain heteroaryl substituted acetone derivatives solve this problem. The present invention thus relates to compounds of formula I

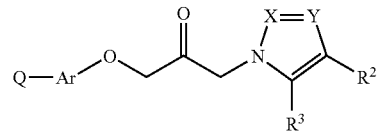

wherein

Q represents R$^1$, OR$^1$, SR$^1$, SOR$^1$, SO$_2$R$^1$, NR$^9$R$^1$ or a straight-chain C$_{1-31}$ alkyl or C$_{2-31}$ alkenyl or alkynyl residue which may be interrupted by 1 or 2 residues, independently selected from O, S, SO, SO$_2$, NR$^9$ and aryl which may be substituted with 1 or 2 substituents R$^4$, and which may be substituted with 1-4 C$_{1-6}$ alkyl residues and/or 1 or 2 aryl residues, wherein the aryl residues may be substituted with 1 or 2 substituents R$^4$;

Ar represents an aryl residue which may be substituted with 1 or 2 R$^4$ substituents;

X represents N or CR$^5$;

Y represents N or CR$^6$;

R$^1$ represents H or an aryl residue which may be substituted with 1 or 2 R$^4$ substituents;

R$^2$ and R$^3$ a) independently represent H, C$_{1-6}$ alkyl, C$_{2-6}$ alkenyl, C$_{2-6}$ alkynyl or R$^7$—W, or b) together with the carbon atoms to which they are bound represent a 5- or 6-membered aromatic or heteroaromatic ring which may be substituted with 1 or 2 R$^4$ substituents;

R$^4$ represents C$_{1-6}$ alkyl, halogen, CF$_3$, CN, NO$_2$, OR$^9$, S(O)$_o$R$^9$, COR$^9$, COOR$^9$, CONR$^9$R$^{10}$, SO$_3$R$^9$, SO$_2$NR$^9$R$^{10}$, tetrazolyl or R$^7$—W;

R$^5$ represents H or R$^4$;

R$^6$ represents H, C$_{1-6}$ alkyl, halogen, CF$_3$, CN, NO$_2$, OR$^9$, SR$^9$, COR$^9$, COOR$^9$, CONR$^9$R$^{10}$, SO$_3$R$^9$, SO$_2$NR$^9$R$^{10}$, tetrazolyl or R$^8$—W;

R$^7$ represents C$_{1-6}$ alkyl, C$_{2-6}$ alkenyl or C$_{2-6}$ alkynyl;

R$^8$ represents C$_{2-6}$ alkyl, C$_{2-6}$ alkenyl or C$_{2-6}$ alkynyl;

R$^9$ represents H, C$_{1-6}$ alkyl or aryl;

R$^{19}$ represents H or C$_{1-6}$ alkyl;

W represents COOH, SO$_3$H or tetrazolyl; and o is 0, 1 or 2;

and the pharmaceutically compatible salts and esters thereof.

The pharmaceutically compatible salts may be base addition salt. They comprise salts of the compounds with inorganic bases, such as alkali hydroxides, alkaline earth hydroxides or with organic bases, such as mono-, di- or triethanolamine. Acid addition salts are also included.

The pharmaceutically compatible esters of the compounds comprise in particular esters which can easily be hydrolyzed physiologically, e.g. alkyl, pivaloyloxymethyl, acetoxymethyl, phthalidyl, indanyl and methoxymethylene esters.

Unless otherwise stated, the expression "alkyl" comprises straight-chain, branched or cyclic alkyl groups, such as methyl, ethyl, propyl, butyl, pentyl, neopentyl, undecyl, dodecyl, pentadecyl, hexadecyl, heptadecyl, octadecyl, cyclohexyl, etc.

The expression "alkenyl" comprises straight-chain, branched or cyclic alkenyl groups, such as ethenyl, propenyl, butenyl, decenyl, heptadecenyl, cyclohexenyl, etc.

The term "alkynyl" comprises straight-chain or branched alkynyl groups, such as ethynyl, propynyl, butynyl, decynyl, heptadecynyl, etc.

The term "aryl" comprises phenyl, naphthyl, biphenyl and 5- or 6-membered heterocyclic rings, containing 1 to 3 atoms selected from O, N or S and optionally anellated using a benzene ring. Phenyl and indolyl, in particular phenyl, are preferred.

The expression "halogen" comprises a fluorine, chlorine, bromine or iodine atom, the fluorine or chlorine atom being particularly preferred.

If residues such as $R^4$, $R^7$, $R^9$ and/or $R^{10}$ occur several times in a compound, they can each be selected independently from one another.

The straight-chain $C_{1-31}$ alkyl or $C_{2-31}$ alkenyl or alkynyl residue, denoted by Q in formula I, can be interrupted by 1 or 2 residues, independently selected from O, S, SO, $SO_2$, $NR^9$ and aryl. "Interrupted" is understood to mean here that in addition to the carbon atoms of its chain the residue may contain such a residue both at any site within the chain and at the end of the chain, i.e. between the carbon chain and Ar. The existing substituents which might additionally be present, where appropriate, in the form of 1-4 $C_{1-6}$ alkyl residues and/or 1 or 2 aryl residues may be bound to any carbon atom of the chain.

In the above described compounds of formula I Q preferably denotes

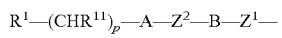

wherein A represents a bond or a straight-chain $C_{1-m}$ alkyl or $C_{2-m}$ alkenyl or alkynyl residue, B represents a bond or a straight-chain $C_{1-n}$ alkyl or $C_{2-n}$ alkenyl or alkynyl residue, $R^1$ and $R^{11}$ independently represent H or an aryl residue, which may be substituted with 1 or 2 substituents $R^4$, and $Z^1$ and $Z^2$ independently represent a bond, O, S, SO, $SO_2$, $NR^9$, $CR^9R^{10}$ or an aryl residue, wherein the aryl residue may be substituted with 1 or 2 substituents $R^4$. p here stands for 0 or 1, m is an integer from 0 to 12 and n for an integer from 0 to 16. The sum of m and n is preferably no greater than 17, in particular no greater than 10.

Q is preferably:

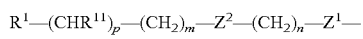

wherein $R^1$, $R^{11}$, $Z^2$, $Z^1$, p, m and n are as defined above.

It is particularly preferred to select Q from:

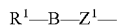

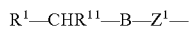

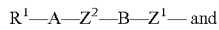

in particular

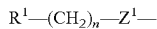

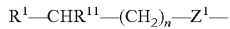

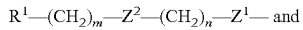 and

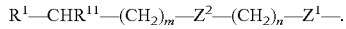

Preferably $R^1$ and $R^{11}$ represent independently from one another, H or a phenyl residue, in particular a non-substituted phenyl residue. If denoting an aryl residue, $Z^1$ and $Z^2$ are preferably phenyl, in particular unsubstituted phenyl.

In a preferred embodiment Q stands for phenyl or $C_{5-12}$ alkyl or alkoxy, more preferably for $C_{7-10}$ alkyl or alkoxy and most preferably for $C_8$ alkyl in den compounds of formula I according to the invention.

In the compounds of formula I according to the invention Ar represents an aryl residue and preferably an aryl residue as defined above. It is particularly preferred for Ar to represent a phenyl residue which preferably links the adjacent groups Q and O in para position.

When $R^2$ and $R^3$ together with the carbon atoms to which they are bound form a 5- or 6-membered aromatic or heteroaromatic ring, this is preferably a benzo ring or a 6-membered aromatic heterocyclic ring having 1 to 3 nitrogen atoms. These rings may be substituted with 1 or 2 substituents $R^4$, an $R^4$ substituent and in particular COOH, $CH_3$, Cl, $OCH_3$, CN, CHO, $COOCH_3$ or $CONH_2$ being preferred.

In the heteroaryl residue of the acetone derivatives according to the invention, Y preferably denotes $CR^6$. $R^5$ and $R^6$ are preferably selected from H, COOH, t-butyl, Cl, CHO, $COCH_3$ or $COOCH_3$.

Particularly suited heteroaryl residues for the acetone derivatives according to the invention are pyrrolyl, pyrazolyl, indolyl, indazolyl, pyrrolyl-2-carboxylic acid, pyrrolyl-3-carboxylic acid, indolyl-2-carboxylic acid, indolyl-3-carboxylic acid, indolyl-4-carboxylic acid, indolyl-5-carboxylic acid, indolyl-6-carboxylic acid, 5-methylindolyl, 5-chloroindolyl, 5-methoxyindolyl, indolyl-5-carbonitrile, indolyl-5-carbaldehyde, indolyl-5-carboxylic acid methyl ester, 3-tert-butylindolyl-5-carboxylic acid, 3-chloroindolyl-5-carboxylic acid, 3-formylindolyl-5-carboxylic acid, 3-acetylindolyl-5-carboxylic acid, 3-methoxycarbonylindolyl-5-carboxylic acid, 3-tert-butylindolyl-6-carboxylic acid and indolyl-5-carbamide.

The compounds according to the invention have proved to be potent phospholipase $A_2$ inhibitors. The compounds are thus usable as drugs for preventing and treating diseases caused or contributorily caused by products or secondary products of this enzyme, such as for treating the rheumatoid diseases and for preventing and treating allergically induced diseases. The compounds according to the invention thus represent inter alia effective analgesics, antiphlogistics, antipyretics, antiallergics and broncholytics and are usable for thrombosis prophylaxis and for the prophylaxis of anaphylactic shock and for treating dermatologic diseases such as psoriasis, urticaria, acute and chronic exanthemas of allergic and non-allergic genesis.

Therefore, the present invention also relates to pharmaceutical preparations comprising a compound of general formula I or a pharmaceutically compatible salt or ester thereof.

The compounds of formula I are particularly suited for the production of a pharmaceutical preparation for preventing or treating diseases which are caused or contributorily caused by an increased activity of phospholipase $A_2$, preferably of cytosolic phospholipase $A_2$. These are e.g. diseases selected from inflammations, pain, fever, allergies, asthma, psoriasis, cerebral ischemia, Alzheimer's disease, chronic skin diseases, damage to the skin caused by U.V. radiation, rheumatic diseases, thrombosis, anaphylactic shock, urticuria, acute and chronic exanthemas and endotoxic shock.

The compounds according to the invention can either be administered as individual therapeutic substances or as mixtures with other therapeutic active substances. They can be administered as such but in general they are given as a pharmaceutical preparation, i.e. as active substance mixtures having suitable pharmaceutical carriers or diluents. The compounds or preparations can be administered orally, parenterally, by inhalation, rectally or topically (including dermally, transdermally, buccally and sublingually).

The kind of pharmaceutical preparation and pharmaceutical carrier or diluent depends on the desired kind of administration. Oral preparations may be present as tablets or capsules, for example, also in a retarded form, and may contain conventional excipients, such as binders (e.g. syrup acacia, gelatin, sorbitol, tragacanth or polyvinylpyrrolidone), fillers (e.g. lactose, sugar, corn starch, calcium phosphate, sorbitol or glycine, lubricants (e.g. magnesium stearate, talcum, polyethylene glycol or silica), disintegrating agents (e.g. starch) or wetting agents (e.g. sodium lauryl sulfate). Oral liquid preparations may be present as aqueous or oily suspensions, solutions, emulsions, syrups, elixirs, or sprays, etc., or may be present as a dry powder for reconstitution with water or another suitable carrier. Such liquid preparations may contain conventional additives, e.g. suspending agents, flavoring agents, diluents, or emulsifiers. For parenteral administration it is possible to use solutions or suspensions with conventional pharmaceutical carriers. For administration by inhalation the compounds may be present in a powdery, aqueous or partially aqueous solution which can be used as an aerosol. Preparations for topical application may be present e.g. as pharmaceutically compatible powders lotions, ointments, creams, gels or as therapeutic systems which contain therapeutically active amounts of the compounds according to the invention.

The necessary dosage depends on the form of pharmaceutical preparation used, on the kind of application, the severity of the symptoms and the special subject (human or animal) which is treated. The treatment is usually started with a dose below the optimum dose. Thereafter, the dose is raised until the optimum effect for the given conditions is achieved. In general, the compounds according to the invention are administered the best in concentrations by which effective actions can be achieved without detrimental or disadvantageous effects occurring. They can be administered as a single dose or in several doses.

The effectiveness of the compounds according to the invention can be determined by the inhibition of cytosolic phospholipase $A_2$. To this end, cytosolic phospholipase $A_2$ is stimulated in intact human thrombocytes with calcium ionophor A23187 so as to trigger the release of arachidonic acid from the membrane phospholipids. In order to prevent the metabolization of the enzyme product arachidonic acid via the cyclooxygenase route and the 12-lipoxygenase route, the dual cyclooxygenase/12-lipoxygenase-inhibitor 5,8,11,14-eicosatetraynoic acid is added. Following purification by means of solid phase extraction, the released arachidonic acid is determined by reversed phase-HPLC using U.V. detection. The inhibition of the enzyme by a test substance follows from the ratio of the arachidonic acid amounts formed in the presence or absence of the test substance. More detailed information on the test system is made in Example 10.

The present invention also relates to a method of producing a compound of formula I, wherein a compound of formula II

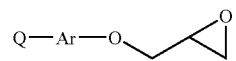

or a compound of formula III

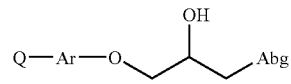

is reacted with a compound of formula IV

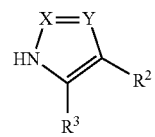

and the alcohol formed is oxidized to give the desired ketone, wherein Q, Ar, X, Y, $R^2$ and $R^3$ are as defined above and Abg stands for a leaving group such as halogen, in particular bromine.

The below examples explain the invention without limiting it to the concrete compounds.

All batches were carried out in a nitrogen protective gas atmosphere. Silica gel 60 of Merck company, Darmstadt, Germany, particle size 63-200 μm or 15-40 μm (=flash chromatography), was used for the column chromatographic purification.

EXAMPLE 1

1-(4-Octylphenoxy)-3-(pyrrol-1-yl)propan-2-one

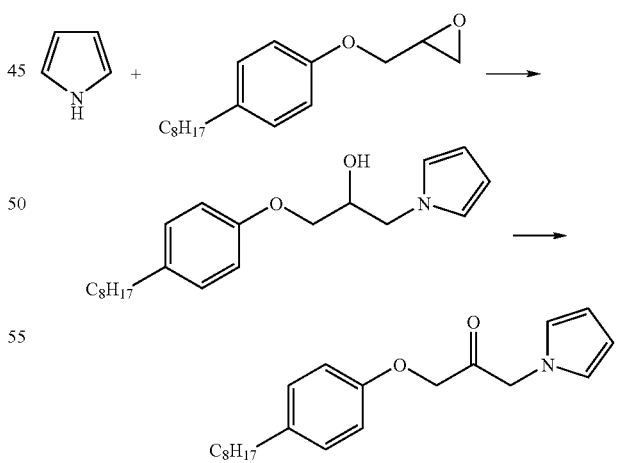

A. 1-(4-Octylphenoxy)-3-(pyrrol-1-yl)propan-2-ol 0.048 g (1.200 mmol) sodium hydride as 60% dispersion in mineral oil is suspended in 10 ml absolute DMF, stirred at room temperature for 10 min and admixed with 0.077 g (1.15 mmol) pyrrole. Having stirred for one hour, a solution of 0.300 g (1.14 mmol) 2-(4-octylphenoxymethyl)oxirane (Kuliev et al. *Uch. Zap. Azerb. Gos. Univ. Ser. Khim Nauk.* 1964, 4, 97; *Chem. Abstr.* 1966, 65, 640c) in 10 ml absolute DMF is added drop-wise. The mixture is stirred for 19 hours, hydrolyzed with a semi-saturated NaCl solution and extracted four times using diethyl ether. The combined organic phases are concentrated to half the volume on the rotary evaporator and washed three times with saturated NaCl solution. Drying on sodium sulfate, filtration and reconcentration on the rotary evaporator leave as a crude product a red oil which is purified on silica gel by means of column chromatography (flow agent: petroleum ether/ethyl acetate 95:5) and yields the product as a yellowish oil.

Yield: 0.229 g (0.695 mmol); 61%

$C_{21}H_{31}NO_2$ (329.5)

$^1$H-NMR (CDCl$_3$): δ (ppm)=0.89 (t, J=7 Hz, 3H), 1.31 (m, 10H), 1.58 (m, 2H), 2.55 (t, J=8 Hz, 2H), 3.83-3.92 (m, 2H), 4.06-4.24 (m, 3H), 6.17 (t, J=2 Hz, 2H), 6.70 (t, J=2 Hz, 2H), 6.82 (d, J=9 Hz, 2H), 7.10 (d, J=9 Hz, 2H)

B. 1-(4-Octylphenoxy)-3-(pyrrol-1-yl)propan-2-one 1.24 g (12.1 mmol) acetic anhydride are mixed with 10 ml absolute DMSO, stirred at room temperature for 10 min and added drop-wise to a solution of 0.100 g (0.304 mmol) 1-(4-octylphenoxy)-3-(pyrrol-1-yl)propan-2-ol in 10 ml absolute DMSO. Having stirred for 19 hours, the solution is poured into a mixture of 5% sodium hydrogen carbonate solution and saturated NaCl solution (1:1, v/v) and hydrolyzed for 10 min. Four extractions with diethyl ether, combination of the organic phases, concentration to half the volume on the rotary evaporator, three wash steps using saturated NaCl solution, drying on sodium sulfate, filtration and reconcentration on the rotary evaporator leave a brownish oil which is purified on silica gel by means of column chromatography (flow agent: petroleum ether/ethyl acetate 97:3) and yields the product as a white solid.

Yield: 0.087 g (0.266 mmol); 88%

Mp.: 58-59° C.

$C_{21}H_{29}NO_2$ (327.5)

$^1$H-NMR (CDCl$_3$): δ (ppm)=0.89 (t, J=7 Hz, 3H), 1.26 (m, 10H), 1.58 (m, 2H), 2.56 (t, J=8 Hz, 2H), 4.59 (s, 2H), 4.97 (s, 2H), 6.24 (t, J=2 Hz, 2H), 6.61 (t, J=2 Hz, 2H), 6.80 (d, J=9 Hz, 2H), 7.12 (d, J=9 Hz, 2H)

EXAMPLE 2

1-(4-Octylphenoxy)-3-(pyrazol-1-yl)propan-2-one

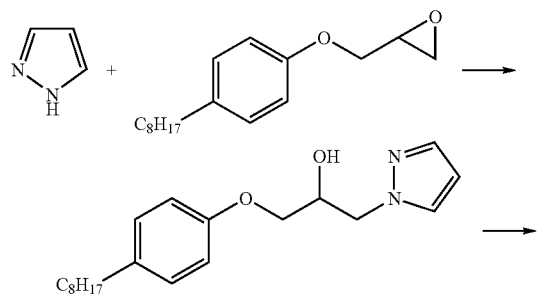

-continued

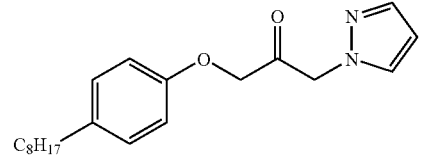

A. 1-(4-Octylphenoxy)-3-(pyrazol-1-yl)propan-2-ol 0.091 g (3.96 mmol) sodium is mixed with 5 ml absolute THF and with a solution of 0.268 g (3.94 mmol) pyrazole in 15 absolute THF. Having stirred at room temperature for 2 hours, a solution of 0.690 g (2.63 mmol) 2-(4-octylphenoxymethyl)oxirane in 10 ml THF is added drop-wise and boiled under reflux for 8 hours. The cooled reaction mixture is poured into semi-saturated NaCl solution and extracted four times using diethyl ether. The combined organic phases are concentrated to half the volume on the rotary evaporator. Washing using a semi-saturated NaCl solution, drying on sodium sulfate, filtration and reconcentration on the rotary evaporator leave as a crude product a yellow solid which is purified on silica gel by means of column chromatography (flow agent: petroleum ether/ethyl acetate 85:15) and recrystallized from petroleum ether and yields the product as a white solid.

Yield: 0.716 g (2.17 mmol); 82%

Mp.: 88° C.

$C_{20}H_{30}N_2O_2$ (330.5)

$^1$H-NMR (CDCl$_3$): δ (ppm)=0.89 (t, J=6 Hz, 3H), 1.28 (m, 10H), 1.58 (m, 2H), 2.55 (t, J=8 Hz, 2H), 3.71-3.78 (m, 1H), 3.92-4.02 (m, 2H), 4.23-4.48 (m, 3H), 6.27 (t, J=2 Hz, 1H), 6.83 (d, J=9 Hz, 2H), 7.09 (d, J=9 Hz, 2H), 7.45 (d, J=2 Hz, 1H), 7.55 (d, J=2 Hz, 1H)

B. 1-(4-Octylphenoxy)-3-(pyrazol-1-yl)propan-2-one 0.154 g (1.51 mmol) acetic anhydride is mixed with 5 ml absolute DMSO, stirred at room temperature for 10 min and added drop-wise to a solution of 0.050 g (0.152 mmol) 1-(4-octylphenoxy)-3-(pyrazol-1-yl)propan-2-ol in 10 ml absolute DMSO. Having stirred at room temperature for 18 hours, the solution is poured into a mixture of 5% sodium hydrogen carbonate solution and saturated NaCl solution (1:1, v/v) and hydrolyzed for 10 min. Four extractions using diethyl ether, combination of the organic phases, concentration to half the volume on the rotary evaporator, three wash steps with saturated NaCl solution, drying on sodium sulfate, filtration and reconcentration on the rotary evaporator leave as a crude product a yellowish solid which is purified on silica gel by means of column chromatography (flow agent: petroleum ether/ethyl acetate 90:10) and yields the product as a white solid.

Yield: 0.048 g (0.146 mmol); 96%

Mp.: 85-87° C.

$C_{20}H_{28}N_2O_2$ (328.5)

$^1$H-NMR (CDCl$_3$): δ (ppm)=0.88 (t, J=7 Hz, 3H), 1.28 (m, 10H), 1.57 (m, 2H), 2.55 (t, J=8 Hz, 2H), 4.63 (s, 2H), 5.26 (s, 2H), 6.36 (t, J=2 Hz, 1H), 6.81 (d, J=9 Hz, 2H), 7.11 (d, J=9 Hz, 2H), 7.43 (d, J=2 Hz, 1H), 7.59 (d, J=2 Hz, 1H)

EXAMPLE 3

1-(Indol-1-yl)-3-(4-octylphenoxy)propan-2-one

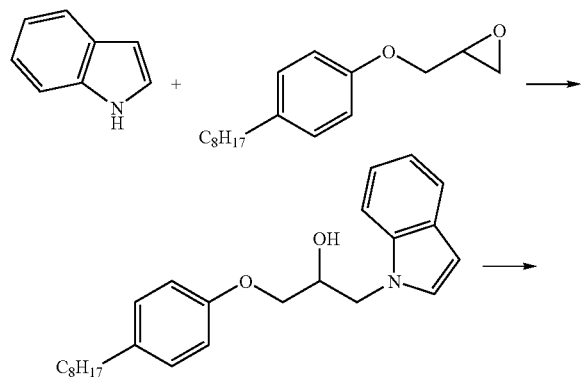

A. 1-(Indol-1-yl)-3-(4-octylphenoxy)propan-2-ol 0.048 g (1.20 mmol) sodium hydride as 60% dispersion in mineral oil are suspended in 10 ml absolute DMF, stirred at room temperature for 10 min and mixed with a solution of 0.134 g (1.14 mmol) indole in 10 ml absolute DMF. Having stirred for 1½ hours, a solution of 0.300 g (1.14 mmol) 2-(4-octylphenoxymethyl)oxirane in 10 ml absolute DMF is added drop-wise. The mixture is stirred for 16 hours, hydrolyzed with a semi-saturated NaCl solution and extracted four times using diethyl ether. The combined organic phases are concentrated to half the volume on the rotary evaporator and washed three times with saturated NaCl solution. Drying on sodium sulfate, filtration and reconcentration on the rotary evaporator leave as a crude product an orange oil which is purified on silica gel by means of column chromatography (flow agent: petroleum ether/ethyl acetate 95:5) and yields the product as a yellow oil.

Yield: 0.356 g (0.938 mmol); 82%

$C_{25}H_{33}NO_2$ (379.5)

$^1$H-NMR (CDCl$_3$): δ (ppm)=0.93 (t, J=7 Hz, 3H), 1.31 (m, 10H), 1.62 (m, 2H), 2.44 (s broad, 1H), 2.58 (t, J=8 Hz, 2H), 3.84-3.94 (m, 2H), 4.29-4.45 (m, 3H), 6.52 (d, J=3 Hz, 1H), 6.82 (d, J=9 Hz, 2H), 7.11 (d, J=9 Hz, 2H), 7.13-7.15 (m, 2H), 7.20-7.25 (m, 1H), 7.40 (d, J=8 Hz, 1H), 7.64 (d, J=8 Hz, 1H)

B. 1-(Indol-1-yl)-3-(4-octylphenoxy)propan-2-one 1.77 g (17.3 mmol) acetic anhydride are mixed with 10 ml absolute DMSO, stirred at room temperature for 10 min and added drop-wise to a solution of 0.164 g (0.432 mmol) 1-(indol-1-yl)-3-(4-octylphenoxy)propan-2-ol in 10 ml absolute DMSO. Having stirred for six hours, the solution is poured into a mixture of 5% sodium hydrogen carbonate solution and saturated NaCl solution (1:1, v/v) and hydrolyzed for 10 min. Four extractions with diethyl ether, combination of the organic phases, concentration to half the volume on the rotary evaporator, three wash steps with saturated NaCl solution, drying on sodium sulfate, filtration and reconcentration on the rotary evaporator leave as a crude product a yellow oil which is purified on silica gel by means of column chromatography (flow agent: petroleum ether/ethyl acetate 95:5) and recrystallized from petroleum ether and yields the product as a white solid.

Yield: 0.106 g (0.281 mmol); 65%

Mp.: 65° C.

$C_{25}H_{31}NO_2$ (377.5)

$^1$H-NMR (CDCl$_3$): δ (ppm)=0.90 (t, J=7 Hz, 3H), 1.30 (m, 10H), 1.59 (m, 2H), 2.57 (t, J=8 Hz, 2H), 4.59 (s, 2H), 5.16 (s, 2H), 6.60 (d, J=3 Hz, 1H), 6.81 (d, J=9 Hz, 2H), 7.05 (d, J=3 Hz, 1H), 7.12-7.16 (m, 4H), 7.19-7.23 (m, 1H), 7.65 (d, J=6 Hz, 1H)

EXAMPLE 4

1-(Indazol-1-yl)-3-(4-octylphenoxy)propan-2-one

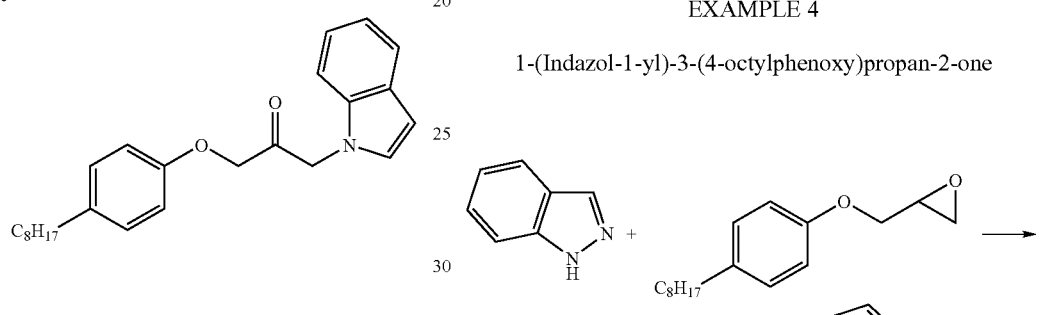

A. 1-(Indazol-1-yl)-3-(4-octylphenoxy)propan-2-ol 0.048 g (1.20 mmol) sodium hydride as a 60% dispersion in mineral oil is suspended in 10 ml absolute DMF, stirred at room temperature for 10 min and mixed with a solution of 0.135 g (1.14 mmol) indazole. Having stirred for 1 hour, a solution of 0.300 g (1.14 mmol) 2-(4-octylphenoxymethyl) oxirane in 10 ml absolute DMF is added drop-wise. The mixture is stirred for 40 hours, hydrolyzed with a semi-saturated NaCl solution and extracted four times using diethyl ether. The combined organic phases are concentrated to half the volume on the rotary evaporator and washed three times with saturated NaCl solution. Drying on sodium sulfate, filtration and reconcentration on the rotary evaporator leave a white solid which is recrystallized from petroleum ether/ethyl acetate (80:20).

B. 1-(Indazol-1-yl)-3-(4-octylphenoxy)propan-2-one 1.07 g (10.5 mmol) acetic anhydride are mixed with 10 ml absolute DMSO, stirred at room temperature for 10 min and added drop-wise to a solution of 0.100 g (0.263 mmol) 1-(indazol-1-yl)-3-(4-octylphenoxy)propan-2-ol in 10 ml absolute DMSO. Having stirred for 20 hours, the solution is poured into a mixture of 5% sodium hydrogen carbonate solution and saturated NaCl solution (1:1, v/v) and hydrolyzed for 10 min. Four extractions using diethyl ether, combination of the organic phases, concentration to half the volume on the rotary evaporator, three wash steps with saturated NaCl solution, drying on sodium sulfate, filtration and reconcentration on the rotary evaporator leave as a crude product a yellow oil which is purified on silica gel by means of column chromatography (flow agent: petroleum ether/ethyl acetate 90:10) and yields the product as a white solid.

Yield: 0.062 g (0.164 mmol)
Mp.: 66-67° C.
$C_{24}H_{30}N_2O_2$ (378.5)
$^1$H-NMR (CDCl$_3$): δ (ppm)=0.88 (t, J=7 Hz, 3H), 1.26 (m, 10H), 1.57 (m, 2H), 2.55 (t, J=8 Hz, 2H), 4.63 (s, 2H), 5.46 (s, 2H), 6.79 (d, J=9 Hz, 2H), 7.11 (d, J=9 Hz, 2H), 7.16-7.20 (m, 2H), 7.37-7.41 (m, 1H), 7.75-7.77 (m, 1H), 8.08 (d, J=1 Hz, 1H)

EXAMPLE 5

1-[3-(4-Octylphenoxy)-2-oxopropyl]pyrrol-2-carboxylic acid

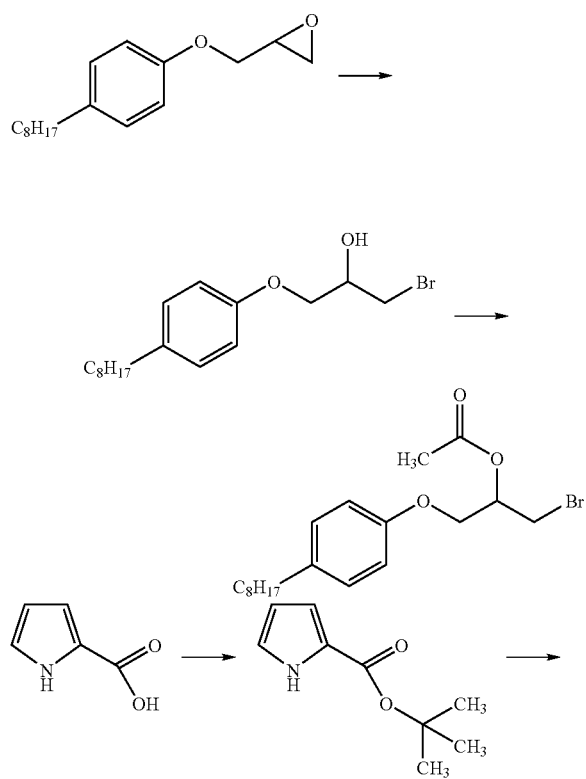

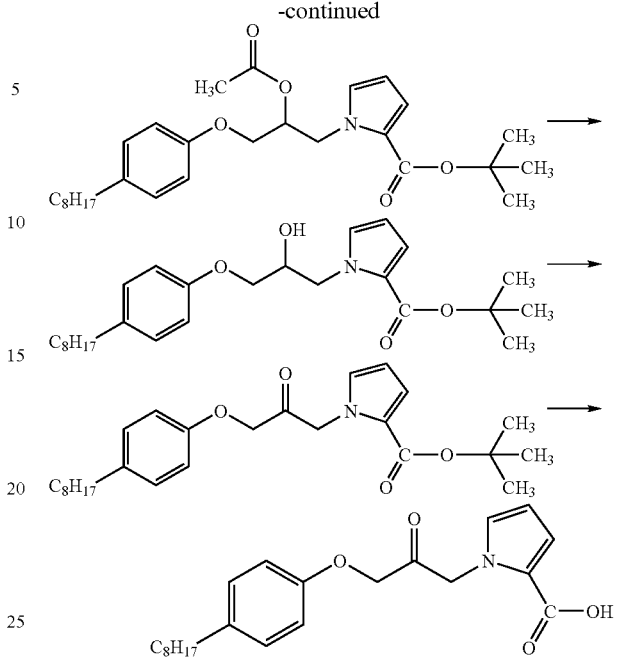

A. 1-Bromo-3-(4-octylphenoxy)propan-2-ol 1.17 g (4.46 mmol) 2-(4-octyl-phenoxymethyl)oxirane are dissolved in 10 ml absolute dichloromethane and mixed with 1.34 g (22.3 mmol) silica gel and with 1.16 g (13.4 mmol) lithium bromide. The suspension is concentrated almost to dryness on the rotary evaporator and allowed to stand at room temperature for 3 hours. The reaction batch is mixed with dichloromethane, filtrated on cotton wool and concentrated on the rotary evaporator. Taking up the suspension in diethyl ether, washing with water, drying on sodium sulfate, filtration and reconcentration on the rotary evaporator yield the product as a yellowish oil.

Yield: 1.52 g (4.42 mmol); 99%
$C_{17}H_{27}BrO_2$ (343.3)
$^1$H-NMR (CDCl$_3$): δ (ppm)=0.89 (t, J=6 Hz, 3H), 1.28 (m, 10H), 1.58 (m, 2H), 2.55 (t, J=8 Hz, 2H), 3.55-3.71 (m, 2H), 4.04-4.21 (m, 3H), 6.84 (d, J=9 Hz, 2H), 7.11 (d, J=9 Hz, 2H)

B. [1-Bromo-3-(4-octylphenoxy)propan-2-yl]acetate 0.41 g (5.18 mmol) absolute pyridine is dissolved in 10 ml absolute dichloromethane, cooled to 0° C. and mixed with 0.41 g (5.22 mmol) acetylchloride, N-aetylpyridiniumchloride precipitating. Having stirred for 30 minutes, 0.50 g (1.46 mmol) 1-bromo-3-(4-octylphenoxy)propan-2-ol is dissolved in 10 ml absolute dichloromethane and added drop-wise. The reaction batch is stirred for another 3 hours at 0° C., diluted with dichloromethane and washed twice with 5% sodium hydrogen carbonate solution. The combined aqueous phases are extracted again with dichloromethane and the combined organic phases are washed with water. Following drying on sodium sulfate, filtration, concentration on the rotary evaporator and mixing with toluene three times and respective concentration on the rotary evaporator, a yellow oil is obtained as the crude product, which is purified by means of column chromatography on silica gel (flow agent: petroleum ether/ethyl acetate 95:5) and yields the product as a yellowish oil.

Yield: 0.56 g (1.45 mmol); 100%

$C_{19}H_{29}BrO_3$ (385.3)

$^1$H-NMR (CDCl$_3$): δ (ppm)=0.89 (t, J=7 Hz, 3H), 1.28 (m, 10H), 1.59 (m, 2H), 2.13 (s, 3H), 2.55 (t, J=8 Hz, 2H), 3.59-3.76 (m, 2H), 4.11-4.18 (m, 2H), 5.31 (m, 1H), 6.86 (d, J=9 Hz, 2H), 7.10 (d, J=9 Hz, 2H)

C. tert-Butylpyrrole-2-carboxylate 0.50 g (4.50 mmol) pyrrole-2-carboxylic acid is suspended in 15 ml absolute benzene and boiled under reflux. A solution of 4.07 g (18.0 mmol) 90% N,N-dimethylformamidedi-tert-butylacetal in 15 ml absolute benzene is added drop-wise within 30 min. Following another heating under reflux for 30 minutes and subsequent cooling, the reaction mixture is diluted with diethyl ether, washed with 5% sodium carbonate solution and with saturated NaCl solution. Drying on sodium sulfate, filtration and concentration on the rotary evaporator leave as the crude product a reddish solid which purified on silica gel by means of column chromatography (flow agent: petroleum ether/ethyl acetate 95:5) yields the product as a white solid.

Yield: 0.566 g (3.38 mmol); 75%

Mp.: 87-89° C.

$C_9H_{13}NO_2$ (167.2)

$^1$H-NMR (CDCl$_3$): δ (ppm)=1.57 (s, 9H), 6.23 (m, 1H), 6.84 (m, 1H), 6.91 (m, 1H), 9.23 (s, broad, 1H)

D. tert-Butyl-1-[2-acetoxy-3-(4-octylphenoxy)propyl]pyrrole-2-carboxylate 0.145 g (0.867 mmol) tert-butylpyrrole-2-carboxylate is dissolved in 10 ml absolute DMSO, mixed with 0.107 g (0.952 mmol) potassium-tert-butylate and stirred at 110° C. for 15 minutes. A solution of 0.333 g (0.864 mmol) [1-bromo-3-(4-octylphenoxy)propan-2-yl]acetate in 10 ml absolute DMSO is added drop-wise. Following heating at 110° C. for 30 minutes and subsequent cooling, hydrolysis is carried out in saturated NaCl solution. Four extractions with diethyl ether, combination of organic phases, concentration to half the volume on the rotary evaporator, three wash steps with saturated NaCl solution, drying on sodium sulfate, filtration and reconcentration on the rotary evaporator leave as the crude product a yellow oil which is purified on silica gel by means of flash column chromatography (flow agent: petroleum ether/ethyl acetate 80:20) and yields the product as a colorless oil.

Yield: 0.169 g (0.358 mmol); 41%

$C_{28}H_{41}NO_5$ (471.6)

$^1$H-NMR (CDCl$_3$): δ (ppm)=0.88 (t, J=7 Hz, 3H), 1.28 (m, 10H), 1.55 (s, 9H), 1.60 (m, 2H), 2.01 (s, 3H), 2.54 (t, J=8 Hz, 2H), 4.01 (dd, J=11 Hz and J=4 Hz, 1H), 4.13 (dd, J=11 Hz and J=4 Hz, 1H), 4.49 (dd, J=14 Hz and J=8 Hz, 1H), 4.86 (dd, J=14 Hz and J=4 Hz, 1H), 5.43-5.48 (m, 1H), 6.07 (dd, J=4 Hz and J=2 Hz, 1H), 6.79-6.83 (m, 3H), 6.88 (dd, J=4 Hz and J=2 Hz, 1H), 7.08 (d, J=9 Hz, 2H)

E. tert-Butyl-1-[2-hydroxy-3-(4-octylphenoxy)propyl]pyrrole-2-carboxylate 0.150 g (0.318 mmol) tert-butyl-1-[2-acetoxy-3-(4-octylphenoxy)propyl]pyrrole-2-carboxylate is dissolved in 10 ml absolute methanol, mixed with 1.26 ml (0.630 mmol) of a 0.5M sodium methanolate solution and stirred at room temperature for 15 min. Following concentration to half the volume on the rotary evaporator, the batch is diluted with diethyl ether. Washing of the organic phase with semi-saturated and with saturated NaCl solution, drying on sodium sulfate, filtration and reconcentration on the rotary evaporator yield the product as a yellowish oil.

Yield: 0.133 g (0.310 mmol); 98%

$C_{26}H_{39}NO_4$ (429.6)

$^1$H-NMR (CDCl$_3$): δ (ppm)=0.89 (t, J=7 Hz, 3H), 1.28 (m, 10H), 1.56 (s, 9H), 1.60 (m, 2H), 2.55 (t, J=8 Hz, 2H), 3.57 (d, J=4 Hz, 1H), 3.93 (d, J=6 Hz, 2H), 4.30 (m, 1H), 4.46 (dd, J=14 Hz and J=6 Hz, 1H), 4.66 (dd, J=14 Hz and J=4 Hz, 1H), 6.11 (dd, J=4 Hz and J=2 Hz, 1H), 6.84 (m, 3H), 6.90 (dd, J=4 Hz and J=2 Hz, 1H), 7.08 (d, J=9 Hz, 2H)

F. tert-Butyl-1-[3-(4-octylphenoxy)-2-oxopropyl]pyrrole-2-carboxylate 1.14 g (11.2 mmol) acetic anhydride are mixed with 10 ml absolute DMSO, stirred at room temperature for 10 min and added drop-wise to a solution of 0.121 g (0.282 mmol) tert-butyl-1-[2-hydroxy-3-(4-octylphenoxy)propyl]pyrrole-2-carboxylate in 10 ml absolute DMSO. Having stirred for 16 hours, the batch is poured into a mixture of 5% sodium hydrogen carbonate solution and saturated NaCl solution (1:1, v/v) and hydrolyzed for 10 min. Four extractions with diethyl ether, combination of the organic phases, concentration to half the volume on the rotary evaporator, three wash steps with saturated NaCl solution, drying on sodium sulfate, filtration and reconcentration on the rotary evaporator leave as a crude product a yellow oil which is purified on silica gel by means of column chromatography (flow agent: petroleum ether/ethyl acetate 98:2) and yields the product as a yellowish oil.

Yield: 0.096 g (0.225 mmol); 80%

$C_{26}H_{37}NO_4$ (427.6)

$^1$H-NMR (CDCl$_3$): δ (ppm)=0.89 (t, J=7 Hz, 3H), 1.29 (m, 10H), 1.52 (s, 9H), 1.60 (m, 2H), 2.55 (t, J=8 Hz, 2H), 4.73 (s, 2H), 5.29 (s, 2H), 6.18 (m, 1H), 6.72 (m, 1H), 6.86 (d, J=8 Hz, 2H), 6.93 (m, 1H), 7.11 (d, J=8 Hz, 2H)

G. 1-[3-(4-Octylphenoxy)-2-oxopropyl]pyrrole-2-carboxylic acid 0.045 g (0.105 mmol) tert-butyl-1-[3-(4-octylphenoxy)-2-oxopropyl]pyrrole-2-carboxylate is dissolved in 10 ml absolute dichloromethane and mixed with 0.900 g (7.89 mmol) trifluoroacetic acid. After stirring at room temperature for 1 hour, the batch is concentrated to dryness on the rotary evaporator. Two dissolutions in toluene and respective concentration on the rotary evaporator leave as a crude product a brownish solid which is recrystallized from methanol and some water drops and yields the product as a beige solid.

Yield: 0.016 g (0.043 mmol); 41%

Mp.: 157° C. (decomp.)

$C_{22}H_{29}NO_4$ (371.5)

$^1$H-NMR (DMSO-d$_6$): δ (ppm)=0.84 (t, J=7 Hz, 3H), 1.24 (m, 10H), 1.50 (s, 2H), 2.49 (t, J=8 Hz, 2H), 4.86 (s, 2H), 5.27 (s, 2H), 6.11 (m, 1H), 6.81 (m, 1H), 6.83 (d, J=8 Hz, 2H), 7.03 (m, 1H), 7.06 (d, J=8 Hz, 2H)

EXAMPLE 6

1-[3-(4-Octylphenoxy)-2-oxopropyl]pyrrole-3-carboxylic acid

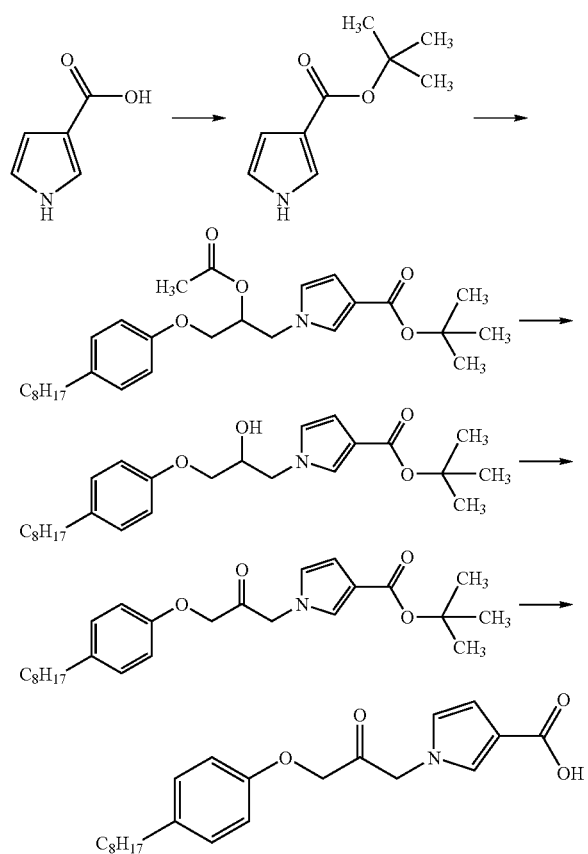

A. tert-Butylpyrrole-3-carboxylate 0.50 g (4.50 mmol) pyrrole-3-carboxylic acid is suspended in 15 ml absolute benzene and boiled under reflux. A solution 4.07 g (18.0 mmol) 90% N,N-dimethylformamidedi-tert-butylacetal in 15 ml absolute benzene is added drop-wise within 30 min. Following another heating under reflux for 30 minutes and subsequent cooling, the reaction mixture is diluted with diethyl ether, washed with 5% sodium carbonate solution and saturated NaCl solution. Drying on sodium sulfate, filtration and concentration on the rotary evaporator leave as a crude product a yellow solid which is purified on silica gel by means of column chromatography (flow agent: petroleum ether/ethyl acetate 90:10) and yields the product as a white solid.

Yield: 0.433 g (2.59 mmol); 58%
Mp.: 82-84° C.
$C_9H_{13}NO_2$ (167.2)
$^1$H-NMR (CDCl$_3$): δ (ppm)=1.55 (s, 9H), 6.59 (m, 1H), 6.72 (m, 1H), 7.34 (m, 1H), 8.75 (s, broad, 1H)

B. tert-Butyl-1-[2-acetoxy-3-(4-octylphenoxy)propyl]pyrrole-3-carboxylate 0.145 g (0.867 mmol) tert-butylpyrrole-3-carboxylate is dissolved in 10 ml absolute DMSO, mixed with 0.107 g (0.952 mmol) potassium-tert-butylate and stirred at 110° C. for 15 min. A solution of 0.333 g (0.864 mmol) [1-bromo-3-(4-octylphenoxy)propan-2-yl]acetate in 10 ml absolute DMSO is added drop-wise. Following 30 minutes of heating at 110° C. and subsequent cooling, hydrolysis is carried out in saturated NaCl solution. Four extractions with diethyl ether, combination of the organic phases, concentration to half the volume on the rotary evaporator, three wash steps using saturated NaCl solution, drying on sodium sulfate, filtration and reconcentration on the rotary evaporator leave as a crude product a yellow oil which is purified on silica gel by means of flash column chromatography (flow agent: petroleum ether/ethyl acetate 93:7) and yields the product as a colorless oil.

Yield: 0.104 g (0.221 mmol); 26%
$C_{28}H_{41}NO_5$ (471.6)
$^1$H-NMR (CDCl$_3$): δ (ppm)=0.88 (t, J=7 Hz, 3H), 1.26 (m, 10H), 1.52 (s, 9H), 1.59 (m, 2H), 2.09 (s, 3H), 2.54 (t, J=8 Hz, 2H), 3.89 (dd, J=10 Hz and J=6 Hz, 1H), 3.95 (dd, J=10 Hz and J=4 Hz, 1H), 3.89-4.25 (m, 2H), 5.30 (m, 1H), 6.50 (dd, J=3 Hz and J=2 Hz, 1H), 6.57 (m, 1H), 6.81 (d, J=9 Hz, 2H), 7.09 (d, J=9 Hz, 2H), 7.20 (m, 1H)

C. tert-Butyl-1-[2-hydroxy-3-(4-octylphenoxy)propyl]pyrrole-3-carboxylate 0.104 g (0.221 mmol) tert-butyl-1-[2-acetoxy-3-(4-octylphenoxy)propyl]pyrrole-3-carboxylate is dissolved in 10 ml absolute methanol, mixed with 0.88 ml (0.440 mmol) of a 0.5M sodium methanolate solution and stirred at room temperature for 15 min. Following concentration to half the volume on the rotary evaporator, the batch is diluted with diethyl ether. Washing of the organic phase with semi-saturated and with saturated NaCl solution, drying on sodium sulfate, filtration and reconcentration on the rotary evaporator yield the product as a yellowish oil.

Yield: 0.091 g (0.212 mmol); 96%
$C_{26}H_{39}NO_4$ (429.6)
$^1$H-NMR (CDCl$_3$): δ (ppm)=0.89 (t, J=7 Hz, 3H), 1.30 (m, 10H), 1.55 (s, 9H), 1.62 (m, 2H), 2.46 (s broad, 1H), 2.54 (t, J=8 Hz, 2H), 3.86 (dd, J=10 Hz and J=6 Hz), 3.92 (dd, J=9 Hz and J=5 Hz), 4.07 (dd, J=14 Hz and J=7 Hz), 4.16 (dd, J=14 Hz and J=5 Hz), 4.27 (m, 1H), 6.55 (dd, J=3 Hz and J=2 Hz, 1H), 6.63 (m, 1H), 6.82 (d, J=9 Hz, 2H), 7.11 (d, J=9 Hz, 2H), 7.27 (m, 1H)

D. tert-Butyl-1-[3-(4-octylphenoxy)-2-oxopropyl]pyrrole-3-carboxylate 0.817 g (8.00 mmol) acetic anhydride is mixed with 10 ml absolute DMSO, stirred at room temperature for 10 min and added drop-wise to a solution of 0.086 g (0.200 mmol) tert-butyl-1-[2-hydroxy-3-(4-octylphenoxy)propyl]pyrrole-3-carboxylate in 10 ml absolute DMSO. Having stirred for 19 hours, the solution is poured into a mixture of 5% sodium hydrogen carbonate solution and saturated NaCl solution (1:1, v/v) and hydrolyzed for 10 min. Four extractions using diethyl ether, combination of the organic phases, concentration to half the volume on the rotary evaporator, three wash steps with saturated NaCl solution, drying on sodium sulfate, filtration and reconcentration on the rotary evaporator leave as a crude product a brown oil which is purified on silica gel by means of flash column chromatography (flow agent: petroleum ether/ethyl acetate 90:10) and yields the product as a yellowish oil.

Yield: 0.065 g (0.152 mmol); 76%

$C_{26}H_{37}NO_4$ (427.6)

$^1$H-NMR (CDCl$_3$): δ (ppm)=0.88 (t, J=7 Hz, 3H), 1.26 (m, 10H), 1.53 (s, 9H), 1.59 (m, 2H), 2.56 (t, J=8 Hz, 2H), 4.63 (s, 2H), 4.99 (s, 2H), 6.50 (m, 1H), 6.59 (dd, J=3 Hz and J=2 Hz, 1H), 6.82 (d, J=9 Hz, 2H), 7.13 (m, 3H)

E. 1-[3-(4-Octylphenoxy)-2-oxopropyl]pyrrole-3-carboxylic acid 0.049 g (0.115 mmol) tert-butyl-1-[3-(4-octylphenoxy)-2-oxopropyl]pyrrole-3-carboxylate is dissolved in 10 ml absolute dichloromethane and mixed with 0.988 g (8.67 mmol) tifluoroacetic acid. Having stirred at room temperature for 3½ hours, the batch is concentrated to dryness on the rotary evaporator. Two dissolution steps in toluene and respective concentrations on the rotary evaporator leave as a crude product a greenish solid which is solved in diethyl ether and precipitated with petroleum ether. Twenty minutes of centrifugation at 3000 rpm, decantation of the supernatant, displacement of the solvent residues in the nitrogen flow and drying in a vacuum desiccator yield the product as a beige solid.

Yield: 0.018 g (0.048 mmol); 42%

Mp.: 125° C. (decomp.)

$C_{22}H_{29}NO_4$ (371.5)

$^1$H-NMR (CDCl$_3$): δ (ppm)=0.88 (t, J=7 Hz, 3H), 1.28 (m, 10H), 1.57 (m, 2H), 2.56 (t, J=8 Hz, 2H), 4.65 (s, 2H), 5.04 (s, 2H), 6.55 (m, 1H), 6.68 (m, 1H), 6.82 (d, J=8 Hz, 2H), 7.14 (d, J=8 Hz, 2H), 7.30 (m, 1H)

EXAMPLE 7

1-[3-(4-Octylphenoxy)-2-oxopropyl]indole-2-carboxylic acid

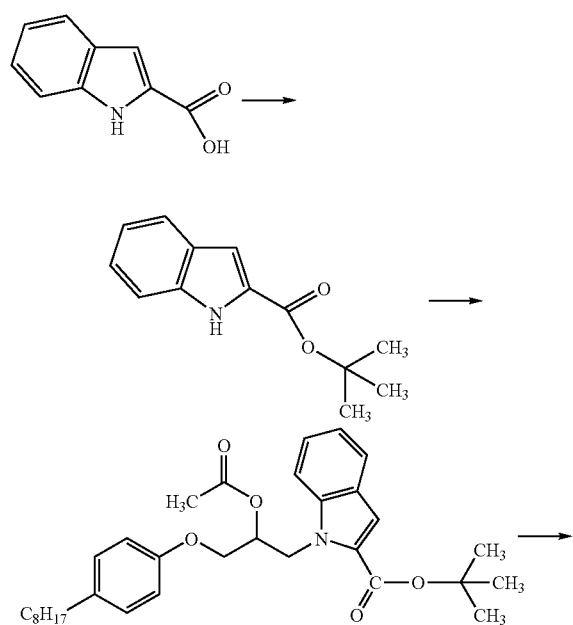

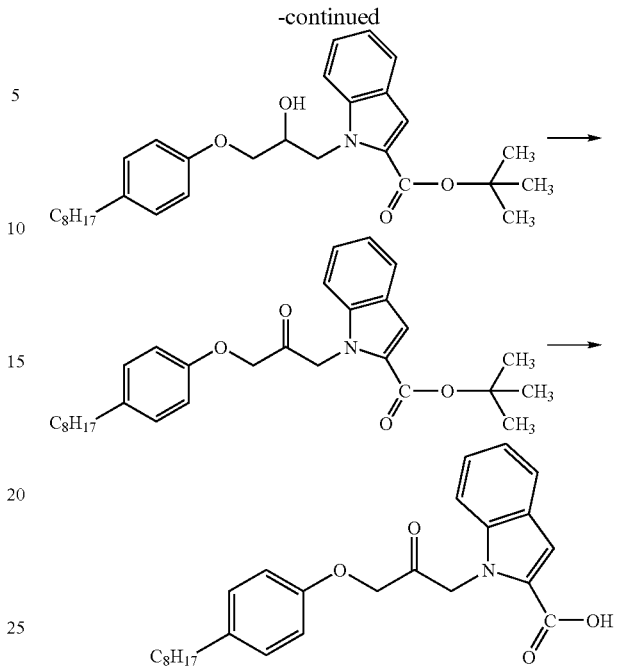

A. tert-Butylindole-2-carboxylate 1.00 g (6.21 mmol) indole-2-carboxylic acid is dissolved in 15 ml absolute THF, mixed with 1.01 g (6.23 mmol) N,N-carbonyldiimidazole and stirred at room temperature for 1 hour. Thereafter, 0.77 g (6.86 mmol) potassium-tert-butylate and 9.12 g (123 mmol) tert-butanol are added. Following heating under reflux for 6 hours, quenching using 5 ml water, filtrating off, rinsing with THF, drying on sodium sulfate and concentration on the rotary evaporator, a brown solid is obtained as the crude product. Preliminary purification by means of column chromatography on silica gel using a short column with petroleum ether/ethyl acetate 95:5 leaves a white solid which is purified on silica gel by means of column chromatography (flow agent: petroleum ether/ethyl acetate 98:2) and yields the product as a white solid.

Yield: 0.325 g (1.496 mmol); 24%

Mp.: 104-105° C.

$C_{13}H_{15}NO_2$ (217.3)

$^1$H-NMR (CDCl$_3$): δ (ppm)=1.65 (s, 9H), 7.14 (m, 2H), 7.31 (m, 1H), 7.43 (dd, J=8 Hz and J=1 Hz, 1H), 7.68 (dd, J=8 Hz and J=1 Hz, 1H), 9.12 (s, broad, 1H)

B. tert-Butyl-1-[2-acetoxy-3-(4-octylphenoxy)propyl]indole-2-carboxylate 0.325 g (1.50 mmol) tert-butylindole-2-carboxylate is dissolved in 15 ml absolute DMSO, mixed with 0.184 g (1.64 mmol) potassium-tert-butylate and stirred at 110° C. for 15 min. A solution of 0.576 g (1.50 mmol) [1-bromo-3-(4-octylphenoxy)propan-2-yl]acetate in 15 ml absolute DMSO is added drop-wise. Following 30 minutes of heating at 110° C. and subsequent cooling, hydrolysis is carried out in saturated NaCl solution. Four extractions with diethyl ether, combination of the organic phases, concentration to half the volume on the rotary evaporator, three wash steps with saturated NaCl solution, drying on sodium sulfate, filtration and reconcentration on the rotary evaporator leave as a crude product a yellow oil which is purified on silica gel by means of flash column chromatography (flow agent: petroleum ether/ethyl acetate 99:1) and yields the product as a colorless oil.

Yield: 0.246 g (0.472 mmol); 32%

$C_{32}H_{43}NO_5$ (521.7)

$^1$H-NMR (CDCl$_3$): δ (ppm)=0.89 (t, J=7 Hz, 3H), 1.30 (m, 10H), 1.59 (m, 2H), 1.62 (s, 9H), 1.81 (s, 3H), 2.56 (t, J=8 Hz, 2H), 4.17 (d, J=4 Hz, 2H), 4.83 (dd, J=15 Hz and J=8 Hz, 1H), 5.07 (dd, J=15 Hz and J=5 Hz, 1H), 5.57 (m, 1H), 6.84 (d, J=9 Hz, 2H), 7.09 (d, J=9 Hz, 2H), 7.13 (m, 1H), 7.26 (s, 1H), 7.32 (m, 1H), 7.57 (d, J=8 Hz, 1H), 7.64 (d, J=8 Hz, 1H)

C. tert-Butyl-1-[2-hydroxy-3-(4-octylphenoxy)propyl]indole-2-carboxylate 0.213 g (0.408 mmol) tert-butyl-1-[2-acetoxy-3-(4-octylphenoxy)propyl]indole-2-carboxylate is dissolved in 10 ml absolute methanol, mixed with 1.64 ml (0.82 mmol) of a 0.5M sodium methanolate solution and stirred at room temperature for 15 min. Following concentration to half the volume on the rotary evaporator, the batch is diluted with diethyl ether. Washing of the organic phase with semi-saturated and with saturated NaCl solution, drying on sodium sulfate, filtration and reconcentration on the rotary evaporator leave as a crude product a yellowish oil which is purified on silica gel by means of column chromatography (flow agent: petroleum ether/ethyl acetate 95:5) and yields the product as a yellowish oil.

Yield: 0.152 g (0.317 mmol); 78%

$C_{30}H_{41}NO_4$ (479.7)

$^1$H-NMR (CDCl$_3$): δ (ppm)=0.89 (t, J=7 Hz, 3H), 1.29 (m, 10H), 1.59 (m, 2H), 1.63 (s, 9H), 2.55 (t, J=8 Hz, 2H), 3.62 (s broad, 1H), 3.99 (dd, J=10 Hz and J=6 Hz, 1H), 4.04 (dd, J=10 Hz and J=5 Hz, 1H), 4.42 (m, 1H), 4.76 (dd, J=15 Hz and J=7 Hz, 1H), 4.81 (dd, J=15 Hz and J=5 Hz, 1H), 6.86 (d, J=9 Hz, 2H), 7.10 (d, J=9 Hz, 2H), 7.14 (m, 1H), 7.29 (m, 2H), 7.48 (d, J=8 Hz, 1H), 7.69 (d, J=8 Hz, 1H)

D. tert-Butyl-1-[3-(4-octylphenoxy)-2-oxopropyl]indole-2-carboxylate 1.02 g (10.0 mmol) acetic anhydride are mixed with 10 ml absolute DMSO, stirred at room temperature for 10 min and added drop-wise to a solution of 0.120 g (0.250 mmol) tert-butyl-1-[2-hydroxy-3-(4-octylphenoxy)propyl]indole-2-carboxylate in 10 ml absolute DMSO. Having stirred for 8 hours, the solution is poured into a mixture of 5% sodium hydrogen carbonate solution and saturated NaCl solution (1:1, v/v) and hydrolyzed for 10 min. Four extractions with diethyl ether, combination of the organic phases, concentration to half the volume on the rotary evaporator, three wash steps using saturated NaCl solution, drying on sodium sulfate, filtration and reconcentration on the rotary evaporator leave as a crude product a yellow oil which is purified on silica gel by means of column chromatography (flow agent: petroleum ether/ethyl acetate 98:2) and yields the product as a yellowish oil.

Yield: 0.113 g (0.237 mmol); 95%

$C_{30}H_{39}NO_4$ (477.6)

$^1$H-NMR (CDCl$_3$): δ (ppm)=0.89 (t, J=7 Hz, 3H), 1.29 (m, 10H), 1.58 (s, 9H), 1.61 (m, 2H), 2.57 (t, J=8 Hz, 2H), 4.73 (s, 2H), 5.57 (s, 2H), 6.87 (d, J=9 Hz, 2H), 7.11-7.14 (m, 4H), 7.30 (m, 2H), 7.68 (d, J=8 Hz, 1H)

E. 1-[3-(4-Octylphenoxy)-2-oxopropyl]indole-2-carboxylic acid 0.046 g (0.096 mmol) tert-butyl-1-[3-(4-octylphenoxy)-2-oxopropyl]indole-2-carboxylate is dissolved in 10 ml absolute dichloromethane and mixed with 1.49 g (13.6 mmol) trifluoroacetic acid. Having stirred at room temperature for 1½ hours, concentration to dryness is carried out on the rotary evaporator. Two dissolution steps in toluene and respective concentration on the rotary evaporator leave as a crude product a yellowish solid which is recrystallized from petroleum ether/ethyl acetate (67:33) and yields the product as a white solid.

Yield: 0.031 g (0.074 mmol); 77%

Mp.: 173° C.

$C_{26}H_{31}NO_4$ (421.5)

$^1$H-NMR (DMSO-d$_6$): δ (ppm)=0.83 (t, J=7 Hz, 3H), 1.23 (m, 10H), 1.50 (m, 2H), 2.48 (t, J=8 Hz, 2H), 4.99 (s, 2H), 5.60 (s, 2H), 6.86 (d, J=9 Hz, 2H), 7.07 (d, J=9 Hz, 2H), 7.12 (m, 1H), 7.26 (s, 1H), 7.29 (m, 1H), 7.54 (d, J=8 Hz, 1H), 7.68 (d, J=8 Hz, 1H)

EXAMPLE 8

1-[3-(4-Octylphenoxy)-2-oxopropyl]indole-3-carboxylic acid

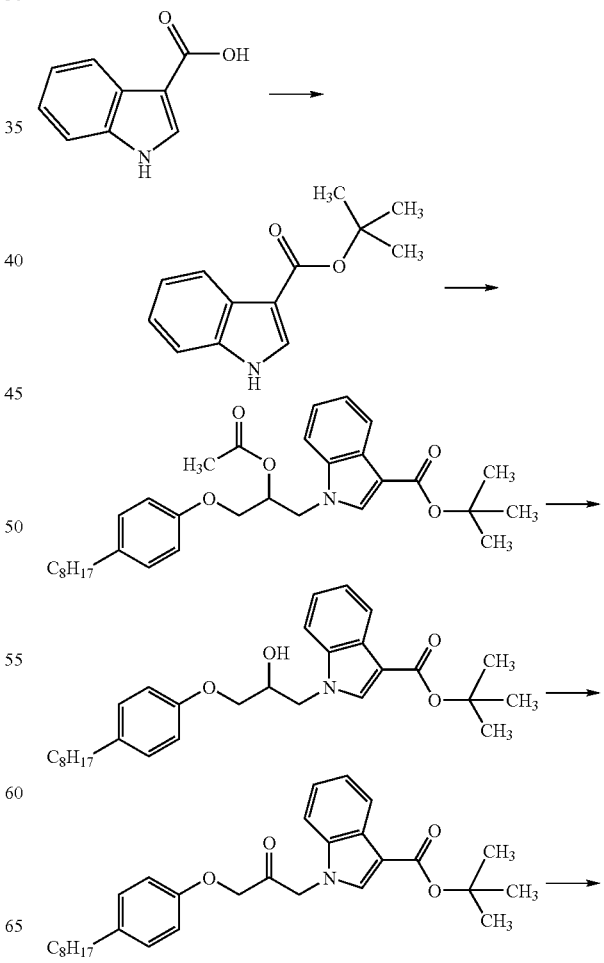

-continued

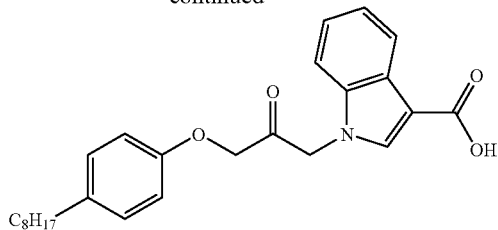

A. tert-Butylindole-3-carboxylate 1.00 g (6.21 mmol) indole-3-carboxylic acid is dissolved in 150 ml absolute THF, mixed with 0.05 g (0.68 mmol) absolute DMF as well as with 1.48 g (12.5 mmol) thionylchloride and stirred at room temperature for 1 hour. Following the drop-wise addition of 2.51 g (24.8 mmol) tiethylamine and of 9.20 g (124 mmol) tert-butanol and heating under reflux for 2 hours, hydrolysis of the cooled reaction mixture is carried out in water. Three extractions with diethyl ether, concentration to half the volume on the rotary evaporator, washing with 5% sodium carbonate solution and with saturated NaCl solution, drying on sodium sulfate, filtration and reconcentration on the rotary evaporator leave as a crude product a brown oil which is purified on silica gel by means of column chromatography (flow agent: petroleum ether/ethyl acetate 90:10) and yields the product as a yellow oil.

Yield: 1.05 g (4.83 mmol); 78%

$C_{13}H_{15}NO_2$ (217.3)

$^1$H-NMR (CDCl$_3$): δ (ppm)=1.65 (s, 9H), 7.25 (m, 2H), 7.39 (m, 1H), 7.85 (d, J=3 Hz, 1H), 8.15 (m, 1H), 8.84 (s, broad, 1H)

B. tert-Butyl-1-[2-acetoxy-3-(4-octylphenoxy)propyl]indole-3-carboxylate 0.50 g (2.30 mmol) tert-butylindole-3-carboxylate is dissolved in 15 ml absolute DMSO, mixed with 0.28 g (2.50 mmol) potassium-tert-butylate and stirred at 110° C. for 15 min. A solution of 0.89 g (2.31 mmol) [1-bromo-3-(4-octylphenoxy)propan-2-yl]acetate in 15 ml absolute DMSO is added drop-wise. Following heating at 110° C. for 30 minutes and subsequent cooling, hydrolysis is carried out in saturated NaCl solution. Four extractions with diethyl ether, combination of the organic phases, concentration to half the volume on the rotary evaporator, three wash steps with saturated NaCl solution, drying on sodium sulfate, filtration and reconcentration on the rotary evaporator leave as a crude product a yellow oil which is purified on silica gel by means of flash column chromatography (flow agent: petroleum ether/ethyl acetate 95:5) and yields the product as a yellowish oil.

Yield: 0.56 g (1.07 mmol); 47%

$C_{32}H_{43}NO_5$ (521.7)

$^1$H-NMR (CDCl$_3$): δ (ppm)=0.89 (t, J=7 Hz, 3H), 1.29 (m, 10H), 1.57 (m, 2H), 1.61 (s, 9H), 2.05 (s, 3H), 2.55 (t, J=8 Hz, 2H), 3.97 (d, J=5 Hz, 2H), 4.51 (dd, J=9 Hz and J=6 Hz, 1H), 4.56 (dd, J=9 Hz and J=6 Hz, 1H), 5.43 (m, 1H), 6.83 (d, J=9 Hz, 2H), 7.10 (d, J=9 Hz, 2H), 7.24 (m, 2H), 7.45 (m, 1H), 7.75 (s, 1H), 8.14 (m, 1H)

C. tert-Butyl-1-[2-hydroxy-3-(4-octylphenoxy)propyl]indole-3-carboxylate 0.293 g (0.562 mmol) tert-butyl-1-[2-acetoxy-3-(4-octylphenoxy)propyl]indole-3-carboxylate is dissolved in 20 ml absolute methanol, mixed with 2.24 ml (1.12 mmol) of a 0.5M sodium methanolate solution and stirred at room temperature for 15 min. Following concentration to half the volume on the rotary evaporator, the batch is diluted with diethyl ether. Washing of the organic phase with semi-saturated and with saturated NaCl solution, drying on sodium sulfate, filtration and reconcentration on the rotary evaporator yield the product as a yellowish oil.

Yield: 0.269 g (0.561 mmol); 100%

$C_{30}H_{41}NO_4$ (479.7)

$^1$H-NMR (CDCl$_3$): δ (ppm)=0.90 (t, J=7 Hz, 3H), 1.30 (m, 10H), 1.59 (m, 2H), 1.63 (s, 9H), 2.56 (t, J=8 Hz, 2H), 2.66 (s, broad, 1H), 3.89 (dd, J=10 Hz and J=5 Hz, 1H), 3.95 (dd, J=10 Hz and J=5 Hz, 1H), 4.30 (dd, J=14 Hz and J=6 Hz, 1H), 4.37 (m, 1H), 4.45 (dd, J=14 Hz and J=4 Hz, 1H), 6.81 (d, J=8 Hz, 2H), 7.09 (d, J=8 Hz, 2H), 7.25 (m, 2H), 7.40 (m, 1H), 7.98 (s, 1H), 8.16 (m, 1H)

D. tert-Butyl-1-[3-(4-octylphenoxy)-2-oxopropyl]indole-3-carboxylate 2.02 g (19.8 mmol) acetic anhydride are mixed with 10 ml absolute DMSO, stirred at room temperature for 10 min and added drop-wise to a solution of 0.237 g (0.494 mmol) tert-butyl-1-[2-hydroxy-3-(4-octylphenoxy)propyl]indole-3-carboxylate in 10 ml absolute DMSO. Having stirred for 2 hours, the solution is poured into a mixture of 5% sodium hydrogen carbonate and saturated NaCl solution (1:1, v/v) and hydrolyzed for 10 min. Four extractions with diethyl ether, combination of the organic phases, concentration to half the volume on the rotary evaporator, three wash steps with saturated NaCl solution, drying on sodium sulfate, filtration and reconcentration on the rotary evaporator leave as a crude product a yellow oil which is purified on silica gel by means of flash column chromatography (flow agent: petroleum ether/ethyl acetate 95:5) and yields the product as a yellowish oil.

Yield: 0.160 g (0.335 mmol); 68%

$C_{30}H_{39}NO_4$ (477.6)

$^1$H-NMR (CDCl$_3$): δ (ppm)=0.89 (t, J=7 Hz, 3H), 1.30 (m, 10H), 1.59 (m, 2H), 1.62 (s, 9H), 2.58 (t, J=8 Hz, 2H), 4.66 (s, 2H), 5.22 (s, 2H), 6.85 (d, J=9 Hz, 2H), 7.08 (dd, J=7 Hz and J=2 Hz, 1H), 7.15 (d, J=9 Hz, 2H), 7.24 (m, 2H), 7.71 (s, 1H), 8.17 (dd, J=6 Hz and J=2 Hz, 1H)

E. 1-[3-(4-Octylphenoxy)-2-oxopropyl]indole-3-carboxylic acid 0.072 g (0.151 mmol) tert-butyl-1-[3-(4-octylphenoxy)-2-oxopropyl]indole-3-carboxylate is dissolved in 10 ml absolute dichloromethane and mixed with 1.56 g (13.7 mmol) trifluoroacetic acid. Having stirred at room temperature for 1 hour, concentration to dryness is carried out on the rotary evaporator. Two dissolution steps in toluene and respective concentration on the rotary evaporator leave as the crude product a reddish solid which is recrystallized from petroleum ether/ethyl acetate (67:33) and yields the product as a white solid.

Yield: 0.055 g (0.130 mmol); 86%

Mp.: 182-183° C.

$C_{26}H_{31}NO_4$ (421.5)

$^1$H-NMR (DMSO-d$_6$): δ (ppm)=0.84 (t, J=7 Hz, 3H), 1.24 (m, 10H), 1.51 (m, 2H), 2.49 (t, J=8 Hz, 2H), 5.00 (s, 2H), 5.46 (s, 2H), 6.88 (d, J=9 Hz, 2H), 7.10 (d, J=9 Hz, 2H), 7.18 (m, 2H), 7.44 (m, 1H), 7.97 (s, 1H), 8.00 (m, 1H)

EXAMPLE 9

1-[3-(4-Octylphenoxy)-2-oxopropyl]indole-5-carboxylic acid

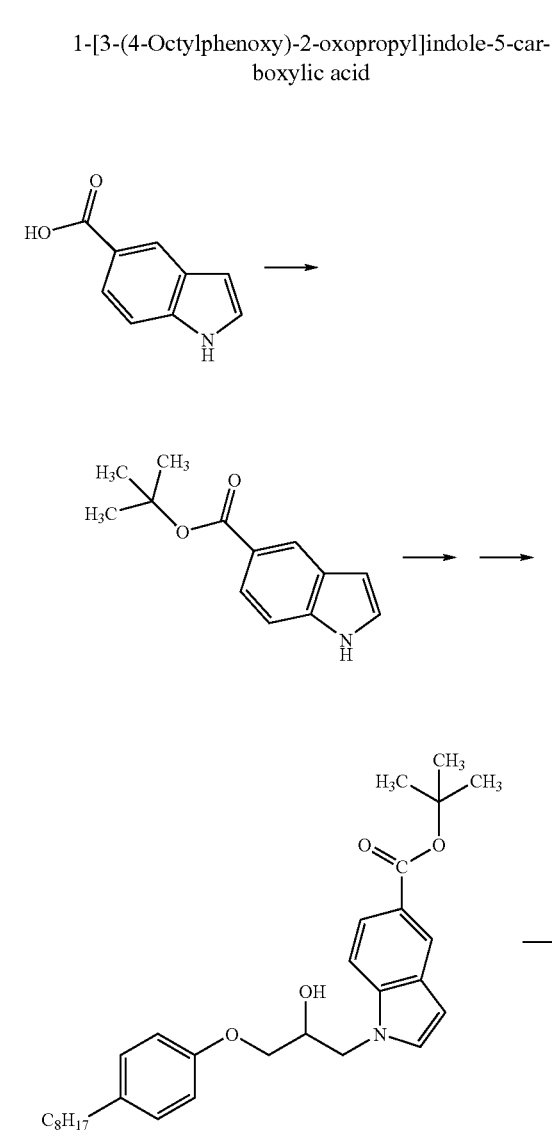

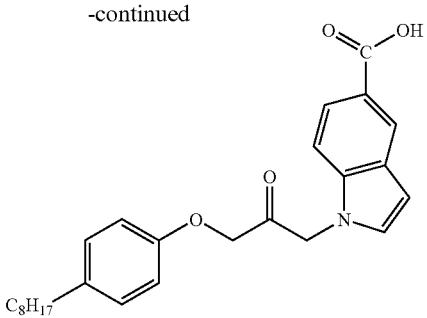

A. tert-Butylindole-5-carboxylate 0.50 g (3.10 mmol) indole-5-carboxylic acid is suspended in 20 ml absolute benzene and heated under reflux. A solution of 2.80 g (12.39 mmol) 90% N,N-dimethylformamidedi-tert-butylacetal in 20 ml absolute benzene is added drop-wise within 30 min. Following another heating under reflux for 30 minutes and subsequent cooling, the reaction mixture is diluted with diethyl ether, washed with 5% sodium carbonate solution and with saturated NaCl solution. Drying on sodium sulfate, filtration and concentration on the rotary evaporator leave as a crude product a yellow oil which is purified on silica gel by means of column chromatography (flow agent: petroleum ether/ethyl acetate 95:5) and yields the product as a white solid.

Yield: 0.214 g (0.98 mmol); 32%

Mp.: 91-93° C.

$C_{13}H_{15}NO_2$ (217.3)

$^1$H-NMR (CDCl$_3$): δ (ppm)=1.63 (s, 9H), 6.64 (m, 1H), 7.26 (m, 1H), 7.38 (d, J=9 Hz, 1H), 7.87 (dd, 1H, J=9 Hz and J=2 Hz), 8.36 (m, 1H), 8.40 (s, broad, 1H)

B. tert-Butyl-1-[2-hydroxy-3-(4-octylphenoxy)propyl]indole-5-carboxylate 0.077 g (1.93 mmol) sodium hydride as a 60% dispersion in mineral oil is suspended in 15 ml absolute DMF, stirred at room temperature for 10 min, mixed with a solution of 0.400 g (1.84 mmol) tert-butylindole-5-carboxylate in 15 ml absolute DMF and stirred at room temperature for one hour. A solution of 0.483 g (1.84 mmol) 2-(4-octyl-phenoxymethyl) oxirane in 15 ml absolute DMF is added drop-wise. Following four hours of heating at 60° C. and subsequent cooling, hydrolysis is carried out in a semi-saturated NaCl solution. Four extractions with diethyl ether, combination of the organic phases, concentration to half the volume on the rotary evaporator, three wash steps with saturated NaCl solution, drying on sodium sulfate, filtration and reconcentration on the rotary evaporator leave as a crude product a yellow oil which is purified on silica gel by means of flash column chromatography (flow agent: petroleum ether/ethyl acetate 90:10) and yields the product as a colorless oil.

Yield: 0.765 g (1.60 mmol); 87%

$C_{30}H_{41}NO_4$ (479.7)

$^1$H-NMR (CDCl$_3$): δ (ppm)=0.89 (t, J=7 Hz, 3H), 1.29 (m, 10H), 1.58 (m, 2H), 1.62 (s, 9H), 2.55 (t, J=8 Hz, 2H), 3.83 (dd, J=10 Hz and J=5 Hz, 1H), 3.93 (dd, J=10 Hz and J=4 Hz, 1H), 4.33 (m, 2H), 4.42 (m, 1H), 6.60 (dd, J=3 Hz and J=1 Hz, 1H), 6.80 (d, J=9 Hz, 2H), 7.08 (d, J=9 Hz, 2H), 7.20 (d, J=3 Hz, 1H), 7.37 (d, J=9 Hz, 1H), 7.86 (dd, J=9 Hz and J=2 Hz, 1H), 8.33 (d, J=2 Hz, 1H)

C. tert-Butyl-1-[3-(4-octylphenoxy)-2-oxopropyl]indole-5-carboxylate 5.33 g (52.2 mmol) acetic anhydride are mixed with 30 ml absolute DMSO, stirred at room temperature for 10 min and added drop-wise to a solution of 0.626 g (1.31 mmol) tert-butyl-1-[2-hydroxy-3-(4-octylphenoxy)propyl]indole-5-carboxylate in 20 ml absolute DMSO. Having stirred for 17 hours, the solution is poured into a mixture of 5% sodium hydrogen carbonate solution and saturated NaCl solution (1:1, v/v) and hydrolyzed for 10 min. Four extractions using diethyl ether, combination of the organic phases, concentration to half the volume on the rotary evaporator, three wash steps with saturated NaCl solution, drying on sodium sulfate, filtration and reconcentration on the rotary evaporator leave as a crude product a yellow oil which is purified on silica gel by means of flash column chromatography (flow agent: petroleum ether/ethyl acetate 95:5) and yields the product as a colorless oil.

Yield: 0.232 g (0.486 mmol); 37%

$C_{30}H_{39}NO_4$ (477.6)

$^1$H-NMR (CDCl$_3$): δ (ppm)=0.89 (t, J=7 Hz, 3H), 1.30 (m, 10H), 1.61 (m, 2H), 1.63 (s, 9H), 2.59 (t, J=8 Hz, 2H), 4.64 (s, 2H), 5.21 (s, 2H), 6.68 (dd, J=3 Hz and J=1 Hz, 1H), 6.84 (d, J=9 Hz, 2H), 7.09 (d, J=9 Hz, 1H and d, J=3 Hz, 1H), 7.15 (d, J=9 Hz, 2H), 7.87 (dd, J=9 Hz and J=2 Hz, 1H), 8.35 (dd, J=2 Hz and J=1 Hz, 1H)

D. 1-[3-(4-Octylphenoxy)-2-oxopropyl]indole-5-carboxylic acid 0.222 g (0.465 mmol) tert-butyl-1-[3-(4-octylphenoxy)-2-oxopropyl]indole-5-carboxylate is dissolved in 60 ml absolute dichloromethane and mixed with 3.98 g (34.9 mmol) trifluoroacetic acid. Having stirred at room temperature for 4 hours, concentration to dryness is carried out on the rotary evaporator. Two admixtures with hexane and respective concentration to dryness on the rotary evaporator leave as a crude product a brownish solid which is purified on an RP-HPLC column by means of chromatography (stationary phase: cromasil, mobile phase acetonitrile/water 80:20) and yields the product as a white solid.

Yield: 0.134 g (0.318 mmol); 68%

Mp.: 122-124° C.

$C_{26}H_{31}NO_4$ (421.5)

$^1$H-NMR (CDCl$_3$): δ (ppm)=0.88 (t, J=7 Hz, 3H), 1.29 (m, 10H), 1.59 (m, 2H), 2.58 (t, J=8 Hz, 2H), 4.66 (s, 2H), 5.25 (s, 2H), 6.71 (d, J=3 Hz, 1H), 6.85 (d, J=8 Hz, 2H), 7.14 (m, 4H), 7.96 (d, J=9 Hz, 1H), 8.49 (s, 1H)

EXAMPLE 10

1-[3-(4-Octylphenoxy)-2-oxopropyl]indole-4-carbocylic acid

A. tert-Butylindol-4-carboxylate

The preparation is based on indol-4-carboxylic acid in analogy to the synthesis of step A of Example 9.

Mp.: 96° C.

$C_{13}H_{15}NO_2$ (217.3)

$^1$H-NMR (CDCl$_3$): δ (ppm)=1.68 (s, 9H), 7.17-7.19 (m, 1H), 7.21-7.25 (m, 1H), 7.33-7.34 (m, 1H), 7.57 (d, J=8 Hz, 1H), 7.88 (dd, J=8 Hz and J=1 Hz, 1H), 8.39 (s, broad, 1H)

B. tert-Butyl-1-[2-hydroxy-3-(4-octylphenoxy)propyl]indole-4-carboxylate

The preparation is based on tert-butylindole-4-carboxylate in analogy to the synthesis of step B of Example 9. Deviating therefrom, the reaction time is only 3 h. Chromatographic purification is initially carried out on silica gel (flow agent petroleum ether/ethyl acetate 85:15) and then on RP18 material (flow agent acetonitrile/water 80:20). The product accrues as an oil.

$C_{30}H_{41}NO_4$ (479.7)

$^1$H-NMR (CDCl$_3$): δ (ppm)=0.88 (t, J=7 Hz, 3H), 1.27-1.31 (m, 10H), 1.56-1.64 (m, 2H), 1.67 (s, 9H), 2.38 (s, broad, 1H), 2.55 (t, J=8 Hz, 2H), 3.83 (dd, J=9 Hz and J=5 Hz, 1H), 3.92 (dd, J=9 Hz and J=5 Hz, 1H), 4.34-4.38 (m, 2H), 4.47 (dd, J=17 Hz and J=8 Hz, 1H), 6.79 (d, J=9 Hz, 2H), 7.08 (d, J=8 Hz, 2H), 7.13 (d, J=3 Hz, 1H), 7.20-7.24 (m, 1H), 7.27 (d, J=3 Hz, 1H), 7.57 (dd, J=8 Hz and J=1 Hz, 1H), 7.86 (d, J=7 Hz, 1H)

C. tert-Butyl-1-[3-(4-octylphenoxy)-2-oxopropyl]indole-4-carboxylate

The preparation is based on tert-butyl-1-[2-hydroxy-3-(4-octylphenoxy)propyl]indole-4-carboxylate in analogy to the synthesis of step C of Example 9. Deviating therefrom, the reaction time is only 15 h. The chromatographic purification is carried out on silica gel (flow agent petroleum ether/ethyl acetate 93:7). The product accrues as a solid.

Mp.: 100° C.

$C_{30}H_{39}NO_4$ (477.6)

$^1$H-NMR (CDCl$_3$): δ (ppm)=0.88 (t, J=7 Hz, 3H), 1.27-1.31 (m, 10H), 1.56-1.60 (m, 2H), 1.67 (s, 9H), 2.57 (t, J=8 Hz, 2H), 4.61 (s, 2H), 5.22 (s, 2H), 6.82 (d, J=9 Hz, 2H), 7.14 (d, J=9 Hz, 2H), 7.16 (d, J=3 Hz, 1H), 7.20-7.22 (m, 2H), 7.24-7.28 (m, 1H), 7.88 (dd, J=7 Hz and J=1 Hz, 1H)

D. 1-[3-(4-Octylphenoxy)-2-oxopropyl]indole-4-carboxylic acid 63 mg (0.13 mmol) ketone are dissolved in 15 ml absolute dichloromethane and mixed with 1.12 g (9.82 mmol) trifluoroacetic acid. Stirring at room temperature for 2 hours is followed by concentration to dryness on the rotary evaporator. Three admixtures with 10 ml of a mixture of petroleum ether and ethyl acetate (1:2) each and respective concentration to dryness on the rotary evaporator leave as a crude product a solid which is recrystallized from petroleum ether/ethyl acetate (2:1).

Yield: 48 mg (0.11 mmol); 86%

Mp.: 160-161° C.

$C_{26}H_{31}NO_4$ (421.5)

$^1$H-NMR (CDCl$_3$): δ (ppm)=0.89 (t, J=7 Hz, 3H), 1.28-1.32 (m, 10H), 1.56-1.63 (m, 2H), 2.58 (t, J=8 Hz, 2H), 4.64 (s, 2H), 5.26 (s, 2H), 6.84 (d, J=9 Hz, 2H), 7.15 (d, J=9 Hz, 2H), 7.22 (d, 1H), 7.25-7.29 (m, 1H), 7.31 (d, J=3 Hz, 1H), 7.35 (d, J=8 Hz, 1H), 8.02 (d, J=7 Hz, 1H)

EXAMPLE 11

1-[3-(4-Octylphenoxy)-2-oxopropyl]indole-6-carboxylic acid

A. tert-Butylindole-6-carboxylate

The preparation is based on indole-6-carboxylic acid in analogy to the synthesis of step A of Example 9. The product is additionally recrystallized from petroleum ether.

Mp.: 100-101° C.

$C_{13}H_{15}NO_2$ (217.3)

$^1$H-NMR (CDCl$_3$): δ (ppm)=1.63 (s, 9H), 6.59 (m, 1H), 7.35 (m, 1H), 7.63 (d, J=8 Hz, 1H), 7.77 (dd, J=8 Hz and J=1 Hz, 1H), 8.13 (m, 1H), 8.55 (s, broad, 1H)

B. tert-Butyl-1-[2-hydroxy-3-(4-octylphenoxy)propyl]indole-6-carboxylate

The preparation is based on tert-butylindole-6-carboxylate in analogy to the synthesis of step B of Example 9. Deviating therefrom, the reaction time is 5 h. The chromatographic purification is initially carried out on silica gel (flow agent: petroleum ether/ethyl acetate 9:1) and then on RP18 material (flow agent acetonitrile/water 4:1). The product accrues as an oil.

$C_{30}H_{41}NO_4$ (479.7)

$^1$H-NMR (CDCl$_3$): δ (ppm)=0.88 (t, J=7 Hz, 3H), 1.26-1.30 (m, 10H), 1.56-1.60 (m, 2H), 1.62 (s, 9H), 2.45 (s, broad, 1H), 2.54 (t, J=8 Hz, 2H), 3.84 (dd, J=10 Hz and J=5 Hz, 1H), 3.93 (dd, J=10 Hz and J=4 Hz, 1H), 4.33-4.37 (m, 2H), 4.48 (dd, J=17 Hz and J=8 Hz, 1H), 6.54 (dd, J=3 Hz and J=1 Hz, 1H), 6.80 (d, J=9 Hz, 2H), 7.08 (d, J=9 Hz, 2H), 7.30 (d, J=3 Hz, 1H), 7.61 (d, J=8 Hz, 1H), 7.75 (dd, J=8 Hz and J=1 Hz, 1H), 8.11 (m, 1H)

C. tert-Butyl-1-[$^3$-(4-octylphenoxy)-2-oxopropyl]indole-6-carboxylate

The preparation is based on tert-butyl-1-[2-hydroxy-3-(4-octylphenoxy)propyl]indole-6-carboxylate in analogy to the synthesis of step C of Example 9. Deviating therefrom, the reaction time is only 16 h. The product accrues as an oil.

$C_{30}H_{39}NO_4$ (477.6)

$^1$H-NMR (CDCl$_3$): δ (ppm)=0.89 (t, J=7 Hz, 3H), 1.27-1.31 (m, 10H), 1.57-1.62 (m, 2H), 1.62 (s, 9H), 2.57 (t, J=8 Hz, 2H), 4.64 (s, 2H), 5.28 (s, 2H), 6.62 (dd, J=3 Hz and J=1 Hz, 1H), 6.84 (d, J=8 Hz, 2H), 7.14 (d, J=8 Hz, 2H), 7.16 (d, J=3 Hz, 1H), 7.63 (dd, J=8 Hz and J=1 Hz, 1H), 7.74 (dd, J=8 Hz and J=1 Hz, 1H), 7.89 (m, 1H)

D. 1-[$^3$-(4-Octylphenoxy)-2-oxopropyl]indole-6-carboxylic acid 59 mg (0.12 mmol) tert-butyl-1-[3-(4-octylphenoxy)-2-oxopropyl]indole-6-carboxylate are dissolved in 15 ml absolute dichloromethane and mixed with 1.05 g (9.20 mmol) trifluoroacetic acid. After stirring at room temperature for 2½ hours, concentration to dryness is carried out on the rotary evaporator. Three admixtures with 10 ml of a mixture of petroleum ether and ethyl acetate (1:2) each and respective concentration to dryness on the rotary evaporator leave as a crude product a solid which is purified on an RP-HPLC column (stationary phase: cromasil, mobile phase: acetonitrile/water 9:1) by means of chromatography.

Yield: 30 mg (0.07 mmol); 57%

Mp.: 180° C.

$C_{26}H_{31}NO_4$ (421.5)

$^1$H-NMR (DMSO-d$_6$): δ (ppm) 0.83 (t, J=7 Hz, 3H), 1.21-1.27 (m, 10H), 1.48-1.62 (m, 2H), 2.48 (t, J=8 Hz, 2H), 5.00 (s, 2H), 5.48 (s, 2H), 6.55 (dd, J=3 Hz and J=1 Hz, 1H), 6.86 (d, J=9 Hz, 2H), 7.08 (d, J=9 Hz, 2H), 7.46 (d, J=3 Hz, 1H), 7.58-7.62 (m, 2H), 8.06 (d, J=1 Hz, 1H)

EXAMPLE 12

1-(5-Methylindol-1-yl)-3-(4-octylphenoxy)propan-2-one

A. 1-(5-Methylindole-1-yl)-3-(4-octylphenoxy)propan-2-ol

The preparation is based on 5-methylindole in analogy to the synthesis of step B of Example 9. Deviating therefrom, the reaction is carried out at room temperature. The reaction time is 23 h. The chromatographic purification is carried out on silica gel (flow agent: petroleum ether/ethyl acetate 95:5). The product accrues as an oil.

$C_{26}H_{35}NO_2$ (393.6)

$^1$H-NMR (CDCl$_3$): δ (ppm)=0.89 (t, J=7 Hz, 3H), 1.27-1.31 (m, 10H), 1.54-1.58 (m, 2H), 2.36 (s, broad, 1H), 2.45 (s, 3H), 2.55 (t, J=8 Hz, 2H), 3.85 (dd, J=10 Hz and J=5 Hz, 1H), 3.98 (dd, J=10 Hz and J=4 Hz, 1H), 4.31 (dd, J=12 Hz and J=7 Hz, 1H), 4.33-4.38 (m, 1H), 4.40 (dd, J=12 Hz and J=5 Hz), 6.42 (dd, J=3 Hz and J=1 Hz, 1H), 6.81 (d, J=9 Hz, 2H), 7.03 (dd, J=8 Hz and J=1 Hz, 1H), 7.08 (d, J=9 Hz, 2H), 7.09 (d, J=3 Hz, 1H), 7.29 (d, J=8 Hz, 1H), 7.41 (m, 1H)

B. 1-(5-Methylindole-1-yl)-3-(4-octylphenoxy)propan-2-one

The preparation is based on 1-(5-methylindole-1-yl)-3-(4-octylphenoxy)propan-2-ol in analogy to the synthesis of step C of Example 9. Deviating therefrom, the reaction time is 19 h. The chromatographic purification on silica gel is carried out with the flow agent petroleum ether/ethyl acetate 97:3. The product accrues as a solid.

M.: 75° C.

$C_{26}H_{33}NO_2$ (391.6)

$^1$H-NMR (CDCl$_3$): δ (ppm)=0.88 (t, J=7 Hz, 3H), 1.27-1.31 (m, 10H), 1.55-1.59 (m, 2H), 2.44 (s, 3H), 2.56 (t, J=8 Hz, 2H), 4.57 (s, 2H), 5.12 (s, 2H), 6.51 (d, J=3 Hz, 1H), 6.79 (d, J=9 Hz, 2H), 7.00-7.02 (m, 3H), 7.11 (d, J=9 Hz, 2H), 7.42-7.43 (m, 1H)

EXAMPLE 13

1-(5-Chloroindol-1-yl)-3-(4-octylphenoxy)propan-2-one

A. 1-(5-Chloroindol-1-yl)-3-(4-octylphenoxy)propan-2-ol

The preparation is based on 5-chloroindole in analogy to the synthesis of step B of Example 9. Deviating therefrom, the reaction is carried out at room temperature. The reaction time is 17 h. The chromatographic purification on silica gel is carried out with the flow agent petroleum ether/ethyl acetate 95:5. The product accrues as an oil.

$C_{25}H_{32}ClNO_2$ (414.0)

$^1$H-NMR (CDCl$_3$): δ (ppm)=0.88 (t, J=7 Hz, 3H), 1.26-1.31 (m, 10H), 1.55-1.59 (m, 2H), 2.36 (s, broad, 1H), 2.55 (t, J=8 Hz, 2H), 3.83 (dd, J=10 Hz and J=5 Hz, 1H), 3.92 (dd, J=10 Hz and J=4 Hz, 1H), 4.27-4.42 (m, 3H), 6.45 (dd, J=3 Hz and J=1 Hz, 1H), 6.80 (d, J=9 Hz, 2H), 7.09 (d, J=9 Hz, 2H), 7.13 (dd, J=9 Hz and J=2 Hz, 1H), 7.16 (d, J=3 Hz, 1H), 7.30 (d, J=9 Hz, 1H), 7.58 (d, J=2 Hz, 1H)

B. 1-(5-Chloroindol-1-yl)-3-(4-octylphenoxy)propan-2-one

The preparation is based on 1-(5-chloroindol-1-yl)-3-(4-octylphenoxy)propan-2-ol in analogy to the synthesis of step C of Example 9. Deviating therefrom, the reaction time is 16 h. The product accrues as a solid and is recrystallized from petroleum ether.

Mp.: 77° C.
$C_{25}H_{30}ClNO_2$ (412.0)
$^1$H-NMR (CDCl$_3$): δ (ppm)=0.89 (t, J=7 Hz, 3H), 1.28-1.32 (m, 10H), 1.56-1.60 (m, 2H), 2.57 (t, J=8 Hz, 2H), 4.61 (s, 2H), 5.17 (s, 2H), 6.52 (dd, J=3 Hz and J=1 Hz, 1H), 6.82 (d, J=9 Hz, 2H), 6.99 (d, J=9 Hz, 1H), 7.05 (d, J=3 Hz, 1H), 7.12-7.15 (m, 3H), 7.60 (d, J=2 Hz, 1H)

EXAMPLE 14

1-(5-Methoxyindol-1-yl)-3-(4-octylphenoxy)propan-2-one

A. 1-(5-Methoxyindol-1-yl)-3-(4-octylphenoxy)propan-2-ol

The preparation is based on 5-methoxyindole in analogy to the synthesis of step B of Example 9. Deviating therefrom, the reaction is carried out at room temperature and in the absence of light. The reaction time is 17 h. The chromatographic purification is carried out on silica gel (flow agent: petroleum ether/ethyl acetate 93:7). The product accrues as an oil.

$C_{26}H_{35}NO_3$ (409.6)
$^1$H-NMR (CDCl$_3$): δ (ppm)=0.89 (t, J=7 Hz, 3H), 1.27-1.31 (m, 10H), 1.55-1.59 (m, 2H), 2.35 (d, J=5 Hz, 1H), 2.55 (t, J=8 Hz, 2H), 3.84 (dd, J=10 Hz and J=5 Hz, 1H), 3.85 (s, 3H), 3.91 (dd, J=10 Hz and J=4 Hz, 1H), 4.27-4.40 (m, 3H), 6.43 (dd, J=3 Hz and J=1 Hz, 1H), 6.80 (d, J=9 Hz, 2H), 6.86 (dd, J=9 Hz and J=3 Hz, 1H), 7.08 (d, J=9 Hz, 2H), 7.09 (d, J=3 Hz, 1H), 7.11 (d, J=3 Hz, 1H), 7.28 (d, J=9 Hz, 1H)

B. 1-(5-Methoxyindol-1-yl)-3-(4-octylphenoxy)propan-2-one

The preparation is based on 1-(5-methoxyindol-1-yl)-3-(4-octylphenoxy)propan-2-ol in analogy to the synthesis of step C of Example 9. Deviating therefrom, the reaction time is 18 h. The reaction is carried in the absence of light. The product accrues as a solid.

Mp.: 85° C.
$C_{26}H_{33}NO_3$ (407.6)
$^1$H-NMR (CDCl$_3$): δ (ppm)=0.88 (t, J=7 Hz, 3H), 1.27-1.31 (m, 10H), 1.55-1.57 (m, 2H), 2.56 (t, J=8 Hz, 2H), 3.85 (s, 3H), 4.56 (s, 2H), 5.12 (s, 2H), 6.51 (dd, J=3 Hz and J=1 Hz, 1H), 6.80 (d, J=9 Hz, 2H), 6.86 (dd, J=9 Hz and J=2 Hz, 1H), 7.01 (d, J=9 Hz, 1H), 7.02 (d, J=3 Hz, 1H), 7.10 (d, J=2 Hz, 1H), 7.12 (d, J=9 Hz, 2H)

EXAMPLE 15

1-(3-(4-Octylphenoxy)-2-oxopropyl]indole-5-carbonitrile

A. 1-[2-Hydroxy-3-(4-octylphenoxy)propyl]indole-5-carbonitrile

The preparation is based on indole-5-carbonitrile in analogy of the synthesis of step B of Example 9. Deviating therefrom, the reaction time is 5 h. The chromatographic purification is initially carried out on silica gel (flow agent: dichloromethane) and then on RP18 material (flow agent acetonitrile/water 75:25). The product accrues as an oil.

$C_{26}H_{32}N_2O_2$ (404.5)
$^1$H-NMR (CDCl$_3$): δ (ppm)=0.89 (t, J=7 Hz, 3H), 1.28-1.32 (m, 10H), 1.55-1.61 (m, 2H), 2.47 (s, broad, 1H), 2.56 (t, J=8 Hz, 2H), 3.85 (dd, J=9 Hz and J=5 Hz, 1H), 3.95 (dd, J=9 Hz and J=4 Hz, 1H), 4.33-4.39 (m, 2H), 4.47 (dd, J=17 Hz and J=7 Hz, 1H), 6.60 (dd, J=3 Hz and J=1 Hz, 1H), 6.83 (d, J=9 Hz, 2H), 7.11 (d, J=9 Hz, 2H), 7.29 (d, J=3 Hz, 1H), 7.41 (dd, J=9 Hz and J=2 Hz, 1H), 7.46 (d, J=9 Hz, 1H), 7.97 (s, 1H)

B. 1-(3-(4-Octylphenoxy)-2-oxopropyl]indole-5-carbonitrile

The preparation is based on 1-[2-hydroxy-3-(4-octylphenoxy)propyl]indole-5-carbonitrile in analogy to the synthesis of step C of Example 9. Deviating therefrom, the reaction time is 15 h. The chromatographic purification on silica gel is carried out with the flow agent petroleum ether/ethyl acetate 90:10. The product accrues as a solid and is recrystallized from petroleum ether/ethyl acetate 95:5.

Mp.: 96° C.
$C_{26}H_{30}N_2O_2$ (402.5)
$^1$H-NMR (CDCl$_3$): δ (ppm)=0.89 (t, J=7 Hz, 3H), 1.28-1.32 (m, 10H), 1.58-1.62 (m, 2H), 2.59 (t, J=8 Hz, 2H), 4.67 (s, 2H), 5.27 (s, 2H), 6.67 (dd, J=3 Hz and J=1 Hz, 1H), 6.85 (d, J=9 Hz, 2H), 7.11 (d, J=9 Hz, 1H), 7.14 (d, J=3 Hz, 1H), 7.16 (d, J=9 Hz, 2H), 7.41 (dd, J=9 Hz and J=2 Hz, 1H), 7.99 (dd, J=2 Hz and J=1 Hz, 1H)

EXAMPLE 16

1-[3-(4-Octylphenoxy)-2-oxopropyl]indole-5-carbaldehyde

A. 1-[2-Hydroxy-3-(4-octylphenoxy)propyl]indole-5-carbaldehyde

The preparation is based on indole-5-carbaldehyde in analogy to the synthesis of step B of Example 9. The chromatographic purification is initially carried out on silica gel (flow agent: dichloromethane) and then on RP18 material (flow agent: acetonitrile/water 4:1). The product accrues as a solid.

M.: 79° C.
$C_{26}H_{33}NO_3$ (407.6)
$^1$H-NMR (CDCl$_3$): δ (ppm)=0.88 (t, J=7 Hz, 3H), 1.26-1.30 (m, 10H), 1.55-1.59 (m, 2H), 2.44 (s, broad, 1H), 2.55 (t, J=8 Hz, 2H), 3.86 (dd, J=10 Hz and J=5 Hz, 1H), 3.96 (dd, J=10 Hz and J=4 Hz, 1H), 4.34-4.40 (m, 2H), 4.48 (dd, J=17 Hz and J=7 Hz, 1H), 6.68 (dd, J=3 Hz and J=1 Hz, 1H), 6.80 (d, J=9 Hz, 2H), 7.09 (d, J=9 Hz, 2H), 7.26 (d, J=3 Hz, 1H), 7.48 (d, J=9 Hz, 1H), 7.76 (dd, J=9 Hz and J=2 Hz, 1H), 8.14 (d, J=1 Hz, 1H), 10.00 (s, 1H)

B. 1-(3-(4-Octylphenoxy)-2-oxopropyl]indole-5-carbaldehyde

The preparation is based on 1-[2-hydroxy-3-(4-octylphenoxy)propyl]indole-5-carbaldehyde in analogy to the synthesis of step C of Example 9. Deviating therefrom, the reaction time is 16 h. The chromatographic purification on silica gel is carried out with the flow agent petroleum ether/ethyl acetate 9:1. The product accrues as a solid.

Mp.: 96° C.
$C_{26}H_{31}NO_3$ (405.5)

¹H-NMR (CDCl₃): δ (ppm)=0.88 (t, J=7 Hz, 3H), 1.28-1.32 (m, 10H), 1.59-1.63 (m, 2H), 2.58 (t, J=8 Hz, 2H), 4.67 (s, 2H), 5.26 (s, 2H), 6.74 (dd, J=3 Hz and J=1 Hz, 1H), 6.85 (d, J=9 Hz, 2H), 7.12 (d, J=3 Hz, 1H), 7.15 (d, J=9 Hz, 2H), 7.16 (d, J=9 Hz, 1H), 7.76 (dd, J=9 Hz and J=1 Hz, 1H), 8.16-8.17 (m, 1H), 10.02 (s, 1H)

EXAMPLE 17

Methyl-1-(3-(4-octylphenoxy)-2-oxopropyl]indole-5-carboxylate

A. Methyl-1-[2-hydroxy-3-(4-octylphenoxy)propyl]indole-5-carboxylate

The preparation is based on methylindole-5-carboxylate in analogy to the synthesis of step B of Example 9. Deviating therefrom, the reaction time is 6 h. The product accrues as a solid.

Mp.: 58° C.

$C_{27}H_{35}NO_4$ (437.6)

¹H-NMR (CDCl₃): δ (ppm)=0.89 (t, J=7 Hz, 3H), 1.27-1.30 (m, 10H), 1.55-1.59 (m, 2H), 2.41 (s, broad, 1H), 2.55 (t, J=8 Hz, 2H), 3.85 (dd, J=10 Hz and J=5 Hz, 1H), 3.93 (s, 3H), 3.95 (dd, J=10 Hz and J=5 Hz, 1H), 4.33-4.39 (m, 2H), 4.43-4.49 (m, 1H), 6.61 (dd, J=3 Hz and J=1 Hz, 1H), 6.80 (d, J=9 Hz, 2H), 7.09 (d, J=9 Hz, 2H), 7.22 (d, J=3 Hz, 1H), 7.40 (d, J=9 Hz, 1H), 7.90 (dd, J=9 Hz and J=2 Hz, 1H), 8.39 (m, 1H)

B. Methyl-1-(3-(4-octylphenoxy)-2-oxopropyl]indole-5-carboxylate

The preparation is based on methyl-1-[2-hydroxy-3-(4-octylphenoxy)propyl]indole-5-carboxylate in analogy to the synthesis of step C of Example 9. Deviating therefrom, the reaction time is 19 h. The product accrues as a solid and is recrystallized (without chromatographic purification) from petroleum ether/ethyl acetate 94:6.

Mp.: 118° C.

$C_{27}H_{33}NO_4$ (435.6)

¹H-NMR (CDCl₃): δ (ppm)=0.88 (t, J=7 Hz, 3H), 1.27-1.31 (m, 10H), 1.57-1.60 (m, 2H), 2.57 (t, J=8 Hz, 2H), 3.92 (s, 3H), 4.63 (s, 2H), 5.22 (s, 2H), 6.67 (dd, J=3 Hz and J=1 Hz, 1H), 6.83 (d, J=9 Hz, 2H), 7.08-7.10 (m, 2H), 7.14 (d, J=9 Hz, 2H), 7.89 (dd, J=9 Hz and J=2 Hz, 1H), 8.39 (m, 1H)

EXAMPLE 18

3-tert-Butyl-1-[3-(4-octylphenoxy)-2-oxopropyl]indole-5-carboxylic acid

The compound accrues in the synthesis of 1-[3-(4-octylphenoxy)-2-oxopropyl]indole-5-carboxylic acid (Example 10) as a by-product and can be separated therefrom in the purification by means of RP-HPLC.

Mp.: 146-147° C.

$C_{30}H_{39}NO_4$ (477.6)

¹H-NMR (CDCl₃): δ (ppm)=0.88 (t, J=6 Hz, 3H), 1.26-1.30 (m, 10H), 1.46 (s, 9H), 1.56-1-60 (m, 2H), 2.57 (t, J=8 Hz, 2H), 4.62 (s, 2H), 5.15 (s, 2H), 6.82 (m, 3H), 7.09 (d, J=9 Hz, 1H), 7.14 (d, J=9 Hz, 2H), 7.93 (dd, J=8 Hz and J=1 Hz, 1H), 8.65 (s, 1H).

EXAMPLE 19

3-Chloro-1-[3-(4-octylphenoxy)-2-oxopropyl]indole-5-carboxylic acid

A. tert-Butyl-3-chloroindole-5-carboxylate

A solution of 389 mg (1.79 mmol) tert-butylindole-5-carboxylate in 12 ml methanol is mixed with 335 mg (2.50 mmol) N-chlorosuccinimide and stirred at room temperature overnight. The methanol is removed by rotation and the resulting residue is taken up in 15 ml ethyl acetate. The organic phase is washed twice with 1M sodium hydrogen carbonate solution, dried on sodium sulfate and concentrated by rotation. Column chromatographic processing of the residue on silica gel (flow agent: hexane/ethyl acetate 9:1) yields a solid.

Yield: 190 mg (0.76 mmol); 42%).

$C_{13}H_{14}ClNO_2$ (251.1)

Mp.: 120° C.

¹H-NMR (CDCl₃): δ (ppm)=1.64 (s, 9H), 7.22 (d, J=1 Hz, 1H), 7.35 (d, J=9 Hz, 1H), 7.90 (d, J=9 Hz, 1H), 8.33 (d, J=1 Hz, 1H), 8.39 (s, 1H)

B. tert-Butyl-3-chloro-1-[2-hydroxy-3-(4-octylphenoxy)propyl]indole-5-carboxylate The preparation is based on tert-butyl-3-chloroindole-4-carboxylate in analogy to the synthesis of step B of Example 9. Deviating therefrom, the reaction time is 8 h. The chromatographic purification on silica gel is carried out with dichloromethane as flow agent. The product accrues as an oil.

$C_{30}H_{40}ClNO_4$ (514.1)

¹H-NMR (CDCl₃): δ (ppm)=0.86 (t, J=7 Hz, 3H), 1.28 (m, 10H), 1.59 (m, 2H), 1.63 (s, 9H), 2.53 (s, broad, 1H), 2.56 (t, J=8 Hz, 2H), 3.83 (dd, J=10 Hz and J=5 Hz, 1H), 3.93 (m, 1H), 4.28-4.40 (m, 2H), 4.28-4.40 (m, 3H), 6.79 (d, J=9 Hz, 2H), 7.09 (d, J=9 Hz, 2H), 7.21 (s, 1H), 7.36 (d, J=9 Hz, 1H), 7.88 (dd, J=9 Hz and J=2 Hz, 1H), 8.30 (d, J=2 Hz, 1H)

C. tert-Butyl-3-chloro-1-[3-(4-octylphenoxy)-2-oxopropyl]indole-5-carboxylate The preparation is based on tert-butyl-3-chloro-1-[2-hydroxy-3-(4-octylphenoxy)propyl]indole-5-carboxylate in analogy to the synthesis of step C of Example 9. The chromatographic purification on silica gel is carried out by means of the flow agent petroleum ether/ethyl acetate 9:1. The product accrues as an oil.

$C_{30}H_{38}ClNO_4$ (512.1)

¹H-NMR (CDCl₃): δ (ppm)=0.89 (t, J=7 Hz, 3H), 1.26 (m, 10H), 1.59 (m, 2H), 1.64 (s, 9H), 2.58 (t, J=8 Hz, 2H), 4.66 (s, 2H), 5.18 (s, 2H), 6.84 (d, J=8 Hz, 2H), 7.06 (m, 2H), 7.16 (d, J=8 Hz, 2H), 7.94 (d, J=9 Hz, 1H), 8.31 (s, 1H)

D. 3-Chloro-1-[3-(4-octylphenoxy)-2-oxopropyl]indole-5-carboxylic acid

The preparation is based on tert-butyl-3-chloro-1-[3-(4-octylphenoxy)-2-oxopropyl]indole-5-carboxylate in analogy to the synthesis of step D of Example 9. The product accrues as a solid and is recrystallized (without chromatographic purification) from hexane/tetrahydrofurane.

Mp.: 157° C.

$C_{26}H_{30}ClNO_4$ (456.0)

¹H-NMR (CDCl₃): δ (ppm)=0.88 (t, J=6 Hz, 3H), 1.28 (m, 10H), 1.62 (m, 2H), 2.58 (t, J=8 Hz, 2H), 4.68 (s, 2H), 5.22 (s, 2H), 6.91 (d, J=8 Hz, 2H), 7.09 (m, 2H), 7.16 (d, J=8 Hz, 2H), 7.97 (d, J=9 Hz, 1H), 8.47 (s, 1H)

EXAMPLE 20

3-Formyl-1-[3-(4-octylphenoxy)-2-oxopropyl]indole-5-carboxylic acid

A. tert-Butyl-3-formylindole-5-carboxylate 0.4 ml (4.87 mmol) oxalylchloride are dissolved in a three-neck flask under nitrogen in 15 ml absolute dichloromethane and cooled to 0° C. Thereafter, 0.4 ml absolute dimethylformamide dissolved in 15 ml absolute dichloromethane is added. The mixture is stirred on ice cooling for 20 minutes, gas generation and the formation of a colorless precipitate being observed. Then, 1.00 g (4.64 mmol) tert-butylindole-5-carboxylate is added and the reaction mixture is allowed to heat to room temperature. Stirring is continued for another 20 min, the suspension is transferred using tetrahydrofurane to a round flask and concentrated on a rotary evaporator. The residue is taken up in 40 ml tetrahydrofurane, mixed with 50 ml 20% sodium acetate solution and heated under reflux for 30 minutes. After cooling down, 30 ml 5% sodium hydrogen carbonate solution are added, extracted three times using ethyl acetate, the volume of the combined organic phases is concentrated to about 150 ml and washed with saturated NaCl solution. The organic phase is dried on sodium sulfate and the solvent is removed on the rotary evaporator. Recrystallization of the crude product from n-hexane/ethyl acetate supplies the product as a solid.

Yield: 0.81 g (3.30 mmol); 71%
$C_{14}H_{15}NO_3$ (245.3)
Mp.: 190° C.
$^1$H-NMR (DMSO-$d_6$): δ (ppm)=1.55 (s, 9H), 7.56 (dd, J=9 Hz and J=1 Hz, 1H), 7.81 (dd, J=9 Hz and J=2 Hz, 1H), 8.39 (d, J=3 Hz, 1H), 8.67 (d, J=2 Hz, 1H), 9.94 (s, broad, 1H), 12.40 (s, broad, 1H)

B. tert-Butyl-3-formyl-1-[2-hydroxy-3-(4-octylphenoxy)propyl]indole-5-carboxylate The preparation is based on tert-butyl-3-formylindole-5-carboxylate in analogy to the synthesis of step B of Example 9. Deviating therefrom, the reaction batch is heated to 120° C. for 12 hours. The chromatographic purification on silica gel is carried out using petroleum ether/ethyl acetate 3:2 as flow agent. The product accrues as an oil.

$C_{31}H_{41}NO_5$ (507.7)
$^1$H-NMR (CDCl$_3$): δ (ppm)=0.88 (t, J=7 Hz, 3H), 1.27 (m, 10H), 1.59 (m, 2H), 1.63 (s, 9H), 2.55 (t, J=8 Hz, 2H), 3.07 (s, broad, 1H), 3.98 (m, 2H), 4.37 (dd, J=14 Hz and J=7 Hz, 1H), 4.51 (m, 1H), 4.54 (dd, J=14 Hz and J=4 Hz, 1H), 6.82 (d, J=9 Hz, 2H), 7.10 (d, J=9 Hz, 2H), 7.41 (d, J=9 Hz, 1H), 7.86 (s, 1H), 7.94 (d, J=9 Hz, 1H), 8.81 (s, 1H), 9.86 (s, 1H)

C. tert-Butyl-3-formyl-1-[3-(4-octylphenoxy)-2-oxopropyl]indole-5-carboxylate

The preparation is based on tert-butyl-3-formyl-1-[2-hydroxy-3-(4-octylphenoxy)propyl]indole-5-carboxylate in analogy to the synthesis of step C of Example 9. Deviating therefrom, the reaction time is 20 h. The chromatographic purification on silica gel is carried out using the flow agent petroleum ether/ethyl acetate 3:2. The product accrues as an oil.

$C_{31}H_{39}NO_5$ (505.3)
$^1$H-NMR (CDCl$_3$): δ (ppm)=0.88 (t, J=7 Hz, 3H), 1.29 (m, 10H), 1.63 (m, 11H), 2.58 (t, J=8 Hz, 2H), 4.71 (s, 2H), 5.33 (s, 2H), 6.87 (d, J=8 Hz, 2H), 7.08 (d, J=9 Hz, 1H), 7.17 (d, J=8 Hz, 2H), 7.72 (s, 1H), 7.95 (d, J=9 Hz, 1H), 8.92 (s, 1H), 10.05 (s, 1H)

D. 3-Formyl-1-[3-(4-octylphenoxy)-2-oxopropyl]indole-5-carboxylic acid

The preparation is based on tert-butyl-3-formyl-1-[3-(4-octylphenoxy)-2-oxopropyl]indole-5-carboxylate in analogy to the synthesis of step D of Example 9. Deviating therefrom, the reaction time is only 3 h. The chromatographic purification by means of RP-HPLC is carried out with the flow agent acetonitrile/water 9:1. The product accrues as a solid Mp.: 193° C.
$C_{27}H_{31}NO_5$ (449.5)
$^1$H-NMR (DMSO-$d_6$): δ (ppm)=0.83 (t, J=7 Hz, 3H), 1.24 (m, 10H), 1.51 (m, 2H), 2.51 (t, J=8 Hz, 2H), 5.03 (s, 2H), 5.58 (s, 2H), 6.90 (d, J=9 Hz, 2H), 7.11 (d, J=9 Hz, 2H), 7.60 (d, J=9 Hz, 1H), 7.86 (dd, J=9 Hz and J=2 Hz, 1H), 8.29 (s, 1H), 8.74 (d, J=2 Hz, 1H), 9.97 (s, 1H)

EXAMPLE 21

3-Acetyl-1-[3-(4-octylphenoxy)-2-oxopropyl]indole-5-carboxylic acid

A. Methyl-3-acetylindole-5-carboxylate

In a three-neck flask, 4.20 ml (9.25 mmol) of a 2.2 M ZnCl$_2$ solution in 20 ml absolute dichloromethane is charged under nitrogen and the solution is cooled to 0° C. using an ice bath. Thereafter, 5.62 ml (8.99 mmol) of a 1.6 M n-butyllithium solution are slowly added drop-wise. The reaction mixture is heated to room temperature, stirred for 1 hour, then admixed with the solution of 1.50 g (8.56 mmol) methylindole-5-carboxylate in 20 ml absolute dichloromethane and stirred again at room temperature for one hour. Thereafter, the batch is cooled to 0° C. and 1.28 ml (18.1 mmol) acetylchloride is carefully added so as to form an orange suspension. The latter is stirred at room temperature for 1 hour. Then, 0.93 g (7.02 mmol) aluminum chloride is added. After another hour of stirring at room temperature, hydrolysis with semi-saturated NaCl solution is carried out and 100 ml ethyl acetate and 20 ml tetrahydrofurane are added. Three extractions are carried out using ethyl acetate, the combined organic phases are washed with saturated NaCl solution and the organic phase is dried on sodium sulfate. The solvent is distilled off. Chromatographic purification of the residue on silica gel (flow agent: hexane/ethyl acetate 3:2) yields the product as a solid.

Yield: 0.70 g (3.23 mmol); 38%
Mp.: 235-236° C.
$C_{12}H_{11}NO_3$ (217.2)
$^1$H-NMR (DMSO-$d_6$): δ (ppm)=2.49 (s, 3H), 3.87 (s, 3H), 7.53 (dd, J=9 Hz and J=1 Hz, 1H), 7.82 (dd, J=9 Hz and J=2 Hz, 1H), 8.43 (d, J=3 Hz, 1H), 8.85 (d, J=1 Hz, 1H), 12.23 (s, broad, 1H)

B. 3-Acetylindole-5-carboxylic acid 0.686 g (3.16 mmol) methyl-3-acetylindole-5-carboxylate are dissolved under heat in 10 ml tetrahydrofurane and 10 ml ethylene glycol and mixed with 7.08 g (0.13 mol) potassium hydroxide. Having stirred under reflux for 30 minutes, the reaction mixture is cooled to room temperature. The tetrahydrofurane is removed on the rotary evaporator and the solution is acidified under ice cooling with 20 ml 6N hydrochloric acid. The precipitated light violet precipitate is sucked off and dried.

Yield: 0.64 g (3.16 mmol)
Mp.: 364° C.
$C_{11}H_{09}NO_3$ (203.2)
$^1$H-NMR (DMSO-$d_6$): δ (ppm)=2.47 (s, 3H), 7.50 (dd, J=9 Hz and J=1 Hz, 1H), 7.86 (dd, J=9 Hz and J=2 Hz, 1H), 8.41 (d, 1H), 8.82 (d, 1H), 12.17 (s, broad, 1H), 12.57 (s, broad, 1H)

C. tert-Butyl-3-acetylindole-5-carboxylate

The preparation is based on 3-acetylindole-5-carboxylic acid in analogy to the synthesis of step A of Example 9. The chromatographic purification on silica gel is carried out with hexane/ethyl acetate 3:2 as flow agent.

Mp.: 214° C.
$C_{15}H_{17}NO_3$ (259.1)
$^1$H-NMR (DMSO-$d_6$): δ (ppm)=1.56 (s, 9H), 2.46 (s, 3H), 7.50 (d, J=8 Hz, 1H), 7.76 (d, J=8 Hz, 1H), 8.40 (s, 1H), 8.78 (s, 1H), 12.17 (s, broad, 1H)

D. tert-Butyl-3-acetyl-1-[2-hydroxy-3-(4-octylphenoxy)propyl]indole-5-carboxylate The preparation is based on tert-butyl-3-acetylindole-5-carboxylate in analogy to the synthesis of step B of Example 9. Deviating therefrom, the reaction batch is heated at 120° C. for 26 h. The chromatographic purification on silica gel is carried out using petroleum ether/ethyl acetate 3:2 as flow agent. The product accrues as an oil.

$C_{32}H_{43}NO_5$ (521.7)
$^1$H-NMR (CDCl$_3$): δ (ppm)=0.88 (t, J=7 Hz, 3H), 1.28 (m, 10H), 1.57 (m, 2H), 1.64 (s, 9H), 2.31 (s, 3H), 2.34 (s, broad, 1H), 2.55 (t, J=8 Hz, 2H), 3.99 (m, 2H), 4.32 (dd, J=14 Hz and J=7 Hz, 1H), 4.50 (m, 1H), 4.53 (dd, J=12 Hz and J=4 Hz, 1H), 6.75 (d, J=9 Hz, 2H), 7.10 (d, J=9 Hz, 2H), 7.38 (d, J=9 Hz, 1H), 7.83 (s, 1H), 7.88 (dd, J=7 Hz and J=3 Hz, 1H), 8.84 (d, J=3 Hz, 1H)

E. tert-Butyl-3-acetyl-1-[3-(4-octylphenoxy)-2-oxopropyl]indole-5-carboxylate The preparation is based on tert-butyl-3-acetyl-1-[2-hydroxy-3-(4-octylphenoxy)propyl]indole-5-carboxylate in analogy to the synthesis of step C of Example 9. The chromatographic purification on silica gel is carried out using the flow agent petroleum ether/ethyl acetate 17:3. The product accrues as an oil.

$C_{32}H_{41}NO_5$ (519.3)
$^1$H-NMR (CDCl$_3$): δ (ppm)=0.88 (t, J=7 Hz, 3H), 1.30 (m, 10H), 1.58 (m, 2H), 1.62 (s, 9H), 2.53 (s, 3H), 2.59 (t, J=8 Hz, 2H), 4.69 (s, 2H), 5.29 (s, 2H), 6.86 (d, J=7 Hz, 2H), 7.07 (d, J=9 Hz, 1H), 7.17 (d, J=7 Hz, 2H), 7.71 (s, 1H), 7.92 (dd, J=9 Hz and J=2 Hz, 1H), 9.00 (d, J=2 Hz, 1H)

F. 3-Acetyl-1-[3-(4-octylphenoxy)-2-oxopropyl]indole-5-carboxylic acid

The preparation is based on tert-butyl-3-acetyl-1-[3-(4-octylphenoxy)-2-oxopropyl]indole-5-carboxylate in analogy to the synthesis of step D of Example 9. The product accrues as a solid and is recrystallized (without chromatographic purification) from hexane/tetrahydrofurane.

Mp.: 197° C.
$C_{28}H_{33}NO_5$ (463.6)
$^1$H-NMR (DMSO-$d_6$): δ (ppm)=0.83 (t, J=7 Hz, 3H), 1.23 (m, 10H), 1.51 (m, 2H), 2.47 (m, 2H), 2.51 (s, 3H), 5.03 (s, 2H), 5.53 (s, 2H), 6.89 (d, J=8 Hz, 2H), 7.10 (d, J=8 Hz, 2H), 7.56 (d, J=9 Hz, 1H), 7.81 (dd, J=9 Hz and J=1 Hz, 1H), 8.33 (s, 1H), 8.83 (d, J=1 Hz, 1H)

EXAMPLE 22

3-Methoxycarbonyl-1-[3-(4-octylphenoxy)-2-oxopropyl]indole-5-carboxylic acid

A. 5-tert-Butyl-3-methylindole-3,5-dicarboxylate 0.70 g (14.3 mmol) sodium cyanide is added to a solution of 0.70 g (2.83 mmol) tert-butyl-3-formylindole-5-carboxylate in 30 ml methanol. A yellow solution forms which is admixed spatula-wise with 4.92 g (57.2 mmol) activated brownstone. Stirring is carried out at room temperature for 48 hours. Having added 80 ml dichloromethane and 5 g Celite, the black suspension is sucked off on a suction filter, the residue is washed with dichloromethane and the filtrate is extracted by shaking for complexing excess cyanide ions with a freshly prepared iron (II) sulfate solution. The organic phase is washed with saturated NaCl solution, dried on sodium sulfate and concentrated. The product is obtained as a solid.

Yield: 0.743 g (2.69 mmol); 94%
Mp: 196° C.
$C_{15}H_{17}NO_4$ (275.3)
$^1$H-NMR (CDCl$_3$): δ (ppm)=1.58 (s, 9H), 3.94 (s, 3H), 7.42 (d, J=9 Hz, 1H), 7.92 (d, 1H), 7.99 (d, 1H), 8.84 (d, J=1 Hz, 1H), 9.36 (s, broad 1H)

B. 5-tert-Butyl-3-methyl-1-[2-hydroxy-3-(4-octylphenoxy)propyl]indole-3,5-dicarboxylate The preparation is based on 5-tert-butyl-3-methylindole-3,5-dicarboxylate in analogy to the synthesis of step B of Example 9. Deviating therefrom, the reaction batch is heated at 120° C. for 14 h. The chromatographic purification on silica gel is carried using petroleum ether/ethyl acetate 7:3 as flow agent. The product accrues as an oil.

$C_{32}H_{43}NO_6$ (537.7)
$^1$H-NMR (CDCl$_3$): δ (ppm)=0.89 (t, J=7 Hz, 3H), 1.28 (m, 10H), 1.57 (m, 2H), 1.62 (s, 9H), 2.55 (t, J=8 Hz, 2H), 2.78 (s, broad, 1H), 3.90 (m, 4H), 3.96 (dd, 1H), 4.37 (m, 2H), 4.47 (dd, J=10 Hz and J=4 Hz, 1H), 6.80 (d, J=7 Hz, 2H), 7.10 (d, J=7 Hz, 2H), 7.40 (d, J=9 Hz, 1H), 7.91 (dd, J=9 Hz and J=2 Hz, 1H), 7.96 (s, 1H), 8.79 (d, J=2 Hz, 1H)

C. 5-tert-Butyl-3-methyl-1-[3-(4-octylphenoxy)-2-oxopropyl]indole-3,5-dicarboxylate The preparation is based on 5-tert-butyl-3-methyl-1-[2-hydroxy-3-(4-octylphenoxy)propyl]indole-3,5-dicarboxylate in analogy to the synthesis of step C of Example 9. The chromatographic purification on silica gel is carried out using the flow agent hexane/ethyl acetate 4:1. The product accrues as an oil.

$C_{32}H_{41}NO_6$ (535.7)
$^1$H-NMR (CDCl$_3$): δ (ppm)=0.89 (t, J=7 Hz, 3H), 1.29 (m, 10H), 1.59 (m, 2H), 1.62 (s, 9H), 2.58 (t, J=7 Hz, 2H), 3.93 (s, 3H), 4.69 (s, 2H), 5.27 (s, 2H), 6.85 (d, J=9 Hz, 2H), 7.06 (dd, J=9 Hz and J=1 Hz, 1H), 7.16 (d, J=9 Hz, 2H), 7.72 (s, 1H), 7.90 (dd, J=9 Hz and J=2 Hz, 1H), 8.83 (dd, J=2 Hz and J=1 Hz, 1H)

D. 3-Methoxycarbonyl-1-[3-(4-octylphenoxy)-2-oxopropyl]indole-5-carboxylic acid The preparation is based on 5-tert-butyl-3-methyl-1-[3-(4-octylphenoxy)-2-oxopropyl]indole-3,5-dicarboxylate in analogy to the synthesis of step D of Example 9. Deviating therefrom, the reaction time is only 2 h. The product accrues as a solid and is recrystallized (without chromatographic purification) from hexane/tetrahydrofurane.

Mp.: 208° C.

$C_{28}H_{33}NO_6$ (479.6)

$^1$H-NMR (DMSO-$d_6$): δ (ppm)=0.83 (t, J=7 Hz, 3H), 1.22 (m, 10H), 1.50 (m, 2H), 2.53 (m, 2H), 3.83 (s, 3H), 5.00 (s, 2H), 5.52 (s, 2H), 6.88 (d, J=9 Hz, 2H), 7.09 (d, J=9 Hz, 2H), 7.57 (d, J=9 Hz, 1H), 7.80 (dd, J=9 Hz and J=2 Hz, 1H), 8.16 (s, 1H), 8.65 (d, J=1 Hz, 1H)

EXAMPLE 23

3-tert-Butyl-1-[3-(4-octylphenoxy)-2-oxopropyl]indole-6-carboxylic acid

The compound accrues in the synthesis of 1-[3-(4-octylphenoxy)-2-oxopropyl]indole-6-carboxylic acid (Example 11) as a by-product and can be separated therefrom by purification using RP-HPLC.

Mp.: 145-146° C.

$C_{30}H_{39}NO_4$ (477.6)

$^1$H-NMR (CDCl$_3$): δ (ppm)=0.89 (t, J=6 Hz, 3H), 1.27-1.30 (m, 10H), 1.46 (s, 9H), 1.58-1.62 (m, 2H), 2.59 (t, J=8 Hz, 2H), 4.64 (s, 2H), 5.23 (s, 2H), 6.86 (d, J=9 Hz, 2H), 6.96 (s, 1H), 7.16 (d, J=9 Hz, 2H), 7.87 (m, 2H), 7.96 (m, 1H)

EXAMPLE 24

1-[3-(4-Decyloxyphenoxy)-2-oxopropyl]indole-5-carboxylic acid

A. tert-Butyl-1-[3-(4-decyloxyphenoxy)-2-hydroxypropyl]indole-5-carboxylate The preparation is based on tert-butylindole-5-carboxylate and 2-(4-decyloxyphenoxymethyl)oxirane in analogy to the synthesis of step B of Example 9. Deviating therefrom, the reaction time is 5 h. The chromatographic purification is initially carried out on silica gel (flow agent: petroleum ether/ethyl acetate 85:15) and then on RP18 material (flow agent acetonitrile/water 4:1). The product accrues as an oil.

$C_{32}H_{45}NO_5$ (523.7)

$^1$H-NMR (CDCl$_3$): δ (ppm)=0.88 (t, J=7 Hz, 3H), 1.27-1.34 (m, 12H), 1.42-1.46 (m, 2H), 1.62 (s, 9H), 1.75 (quin, J=7 Hz, 2H), 2.45 (s, broad, 1H), 3.79 (dd, J=10 Hz and J=5 Hz, 1H), 3.88-3.91 (m, 3H), 4.32-4.36 (m, 2H), 4.43 (dd, J=16 Hz and J=8 Hz, 1H), 6.59 (dd, J=3 Hz and J=1 Hz, 1H), 6.78-6.85 (m, 4H), 7.19 (d, J=3 Hz, 1H), 7.36 (d, J=9 Hz, 1H), 7.85 (dd, J=9 Hz and J=2 Hz, 1H), 8.32 (m, 1H)

B. tert-Butyl-1-[3-(4-decyloxyphenoxy)-2-oxopropyl]indole-5-carboxylate

The preparation is based on tert-butyl-1-[3-(4-decyloxyphenoxy)-2-hydroxypropyl]indole-5-carboxylate in analogy to the synthesis of step C of Example 9. The chromatographic purification on silica gel is carried out using the flow agent petroleum ether/ethyl acetate 9:1. The product accrues as a solid.

$C_{32}H_{43}NO_5$ (521.7)

$^1$H-NMR (CDCl$_3$): δ (ppm)=0.88 (t, J=7 Hz, 3H), 1.27-1.34 (m, 12H), 1.41-1.45 (m, 2H), 1.62 (s, 9H), 1.77 (quin, J=7 Hz, 2H), 3.91 (t, J=7 Hz, 2H), 4.59 (s, 2H), 5.21 (s, 2H), 6.67 (d, J=3 Hz, 1H), 6.82-6.87 (m, 4H), 7.08 (d, J=3 Hz, 1H), 7.09 (d, J=9 Hz, 1H), 7.86 (dd, J=9 Hz and J=2 Hz, 1H), 8.34 (d, J=1 Hz, 1H)

C. 1-[3-(4-Decyloxyphenoxy)-2-oxopropyl]indole-5-carboxylic acid 50 mg (0.096 mmol) tert-butyl-1-[3-(4-decyloxyphenoxy)-2-oxopropyl]indole-5-carboxylate are dissolved in 15 ml absolute dichloromethane and mixed with 0.82 g (7.19 mmol) trifluoroacetic acid. Having stirred at room temperature for 4 hours, the batch is concentrated to dryness on the rotary evaporator. Three admixtures with 10 ml of a mixture of petroleum ether and ethyl acetate (4:1) each and respective concentration to dryness on the rotary evaporator leave as a crude product a solid which is purified on an RP-HPLC column by means of chromatography (stationary phase: cromasil, flow agent: acetonitrile/water 90:10).

Yield: 25 mg (0.05 mmol); 56%

Mp.: 137° C.

$C_{28}H_{35}NO_5$ (465.6)

$^1$H-NMR (CDCl$_3$): δ (ppm)=0.89 (t, J=7 Hz, 3H), 1.28-1.33 (m, 12H), 1.43-1.49 (m, 2H), 1.75-1.82 (m, 2H), 3.93 (t, J=7 Hz, 2H), 4.63 (s, 2H), 5.25 (s, 2H), 6.72 (dd, J=3 Hz and J=1 Hz, 1H), 6.84-6.89 (m, 4H), 7.12 (d, J=3 Hz, 1H), 7.14 (d, J=9 Hz, 1H), 7.97 (dd, J=9 Hz and J=2 Hz, 1H), 8.50 (d, J=1 Hz, 1H)

EXAMPLE 25

1-[3-(4-Octylphenoxy)-2-oxopropyl]indole-5-carbamide

A. 1-[2-Hydroxy-3-(4-octylphenoxy)propyl]indole-5-carbamide 0.18 g (0.44 mmol) 1-[2-hydroxy-3-(4-octylphenoxy)propyl]indole-5-carbonitrile (Example 15A) is dissolved in 15 ml tert-butanol, mixed with 0.23 g (3.6 mmol) pulverized, 88% potassium hydroxide and heated under reflux for 11 h. Having cooled down, the mixture is hydrolyzed in water and acidified with 1N hydrochloric acid. Three extractions with diethyl ether, concentration to half the volume on the rotary evaporator, washing with water and with saturated NaCl solution, drying on sodium sulfate, filtration and reconcentration on the rotary evaporator leave as a crude product a yellowish solid which is purified on silica gel by means of column chromatography (flow agent: petroleum ether/ethyl acetate 1:1) and yields the product as a solid.

Yield: 0.13 g (0.31 mmol); 70%

Mp.: 118-119° C.

$C_{26}H_{34}N_2O_3$ (422.6)

$^1$H-NMR (CDCl$_3$): δ (ppm)=0.88 (t, J=7 Hz, 3H), 1.26-1.30 (m, 10H), 1.55-1.58 (m, 2H), 2.52 (m, 2H), 3.85 (dd, J=10 Hz and J=5 Hz, 1H), 3.94 (dd, J=10 Hz and J=4 Hz, 1H), 4.32-4.39 (m, 2H), 4.46 (dd, J=17 Hz and J=8 Hz, 1H), 5.40-6.28 (s, broad, 2H), 6.59 (d, J=3 Hz, 1H), 6.80 (d, J=9 Hz, 2H), 7.09 (d, J=9 Hz, 2H), 7.23 (d, J=3 Hz, 1H), 7.42 (d, J=9 Hz, 1H), 7.66 (d, J=9 Hz, 1H), 8.12 (s, 1H)

B. 1-[3-(4-Octylphenoxy)-2-oxopropyl]indole-5-carbamide

The preparation is based on 1-[2-hydroxy-3-(4-octylphenoxy)propyl]indole-5-carbamide in analogy to the synthesis of step C of Example 9. Deviating therefrom, the reaction time is 19 h. The chromatographic purification on silica gel is carried out using the flow agent petroleum ether/ethyl acetate 1:1. The product accrues as a solid.

M.: 162-163° C.

$C_{26}H_{32}N_2O_3$ (420.5)

$^1$H-NMR (DMSO-$d_6$): δ (ppm)=0.84 (t, J=7 Hz, 3H), 1.23-1.26 (m, 10H), 1.49-1.53 (m, 2H), 2.47-2.51 (m, 2H), 4.97 (s, 2H), 5.39 (s, 2H), 6.54 (d, J=3 Hz, 1H), 6.85 (d, J=9 Hz, 2H), 7.07-7.10 (m, 3H), 7.33 (d, J=3 Hz, 1H), 7.38 (d, J=9 Hz, 1H), 7.65 (d, J=9 Hz, 1H), 7.83 (s, broad, 1H), 8.13 (s, 1H)

EXAMPLE 26

1-[3-(4-Heptyloxyphenoxy)-2-oxopropyl]indole-5-carbamide

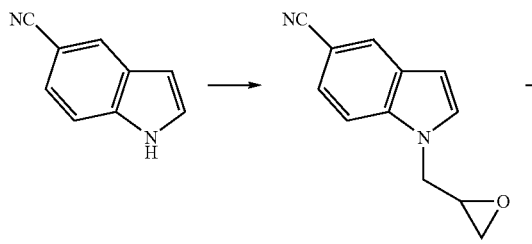

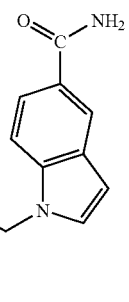

A. 1-Oxiranylmethylindole-5-carbonitrile 2.07 g (42 mmol) pulverized, 88% potassium hydroxide, 3.0 g (0.021 mol) indole-5-carbonitrile and 0.68 g (2 mmol) tetrabutylammoniumbromide are jointly weighed out in the given order and mixed with 9.9 ml (126 mmol) epichlorohydrine with stirring. Stirring is continued overnight. Following hydrolysis and three extractions using ethyl acetate, the combined organic phases are washed three times with water. Drying of the organic phase using sodium sulfate and concentration of the solvent on the rotary evaporator leaves a solid which is purified on silica gel by column chromatography (flow agent: hexane/ethyl acetate 7:3).

Yield: 3.34 g (17 mmol); 80%

Mp.: 92° C.

$C_{12}H_{10}N_2O$ (198.2)

$^1$H-NMR (CDCl$_3$): δ (ppm)=2.29 (dd, J=5 Hz and J=3 Hz, 1H), 2.77 (m, 1H), 3.22 (m, 1H), 4.08 (dd, J=15 Hz and J=6 Hz, 1H), 4.47 (dd, J=15 Hz and J=3 Hz, 1H), 6.54 (d, J=3 Hz, 1H), 7.20 (d, J=3 Hz, 1H), 7.40 (m, 2H), 7.92 (s, 1H)

B. 1-[3-(4-Heptyloxyphenoxy)-2-hydroxypropyl]indole-5-carbonitrile 0.13 g (2.47 mmol) sodium hydride as 60% dispersion in mineral oil is suspended in 10 ml absolute DMF under nitrogen, stirred at room temperature for 10 min and mixed with the solution of 0.5 g (2.39 mmol) 4-heptyloxyphenol in 5 ml absolute DMF. Having stirred for 1 hour, a solution of 475 mg (2.39 mmol) 1-oxiranylmethylindole-5-carbonitrile in 5 ml absolute DMF is added and stirring is continued at room temperature overnight. Thereafter, the suspension is hydrolyzed with semi-saturated NaCl solution and extracted three times with ethyl acetate. The extracts are washed with saturated NaCl solution, dried on sodium sulfate and the solvent is distilled off. The residue is purified on silica gel by means of column chromatography (flow agent: hexane/ethyl acetate 1:1), the product accruing as an oil.

Yield: 0.48 g (1.18 mmol); 49%

$C_{25}H_{30}N_2O_3$ (406.5)

MS (EI): m/z (%)=406 (100) M$^+$, 309 (20), 308 (92), 199 (62), 181 (25), 156 (36), 155 (60), 110 (69)

C. 1-[3-(4-Heptyloxyphenoxy)-2-hydroxypropyl]indole-5-carbamide 455 mg (1.12 mmol) 1-[3-(4-Heptyloxyphenoxy)-2-hydroxypropyl]indole-5-carbonitrile are dissolved in 10 ml tert-butanol. Having added 1.10 g (22.4 mmol) pulverized, 88% potassium hydroxide, the batch is heated to 100° C. for 3 hours. After cooling the reaction solution, hydrolysis using 50 ml distilled water and neutralization with 1 N hydrochloric acid are carried out. The aqueous phase is extracted three times with ethyl acetate and the combined organic phases are washed once with water and then twice with saturated sodium chloride solution. Following drying on sodium sulfate, the solvent is removed on the rotary evaporator. The residue is purified on silica gel by means of column chromatography (flow agent: ethyl acetate), the product accruing as a solid.

Yield: 245 mg (0.58 mmol); 52%

Mp.: 114° C.

$C_{25}H_{32}N_2O_4$ (424.5)

MS (EI): m/z (%)=424 (67) M$^+$, 328 (21), 327 (100), 174 (18), 173 (69)

D. 1-[3-(4-Heptyloxyphenoxy)-2-oxopropyl]indole-5-carbamide

The preparation is based on 1-[3-(4-heptyloxyphenoxy)-2-hydroxypropyl]indole-5-carbamide in analogy to the synthesis of step C of Example 9. Deviating therefrom, the reaction time is 20 h. The product is extracted from the reaction batch by means of ethyl acetate. The chromatographic purification on silica gel is carried out with the flow agent ethyl acetate. Following recrystallization from hexane/ethyl acetate, the product accrues as a solid.

M.: 157° C.

$C_{25}H_{30}N_2O_4$ (422.5)

$^1$H-NMR (DMSO-d$_6$): δ (ppm)=0.82 (t, J=7 Hz, 3H), 1.20-1.36 (m, 6H), 1.37-1.42 (m, 2H), 1.62 (quin, J=7 Hz, 2H), 3.87 (t, J=7 Hz, 2H), 4.93 (s, 2H), 5.39 (s, 2H), 6.54 (d, J=3 Hz, 1H), 6.82-6.93 (m, 4H), 7.21 (s, 1H), 7.37 (d, J=3 Hz, 1H), 7.41 (d, J=8 Hz, 1H), 7.66 (dd, J=8 Hz and J=2 Hz, 1H), 7.82 (s, 1H), 8.19 (d, J=2 Hz, 1H)

EXAMPLE 27

1-[3-(Biphenyl-4-yloxy)-2-oxopropyl]indole-5-carbamide

A. 1-[3-(Biphenyl-4-yloxy)-2-hydroxypropyl]indole-5-carbonitrile 0.34 g (2.02 mmol) 4-phenyl phenol are dissolved in 5 ml absolute THF under nitrogen and mixed drop-wise with 0.1 ml (1.0 mmol) tert-butyllithium with constant stirring. The mixture is stirred at room temperature for 5 min. Thereafter, the solution of 0.20 g (1.0 mmol) 1-oxiranylmethylindole-5-carbonitrile (Example 26A) in 5 ml absolute THF is added drop-wise. The batch is heated at 100° C. for 4 hours. Having cooled down, the batch is mixed with 100 ml diethyl ether and extracted three times using water. The aqueous phase is extracted twice using ethyl acetate and the combined organic phases are dried on sodium sulfate, filtrated and the solvent is removed in vacuo. The residue is purified on silica gel by means of column chromatography (flow agent: hexane/ethyl acetate 7:3). The product is obtained as a solid.

Yield: 0.37 g (1.0 mmol); 100%

Mp.: 133° C.

$C_{24}H_{20}N_2O_2$ (368.4)

$^1$H-NMR (DMSO-d$_6$): δ (ppm)=3.90-3.92 (m, 2H), 4.20 (m, 1H), 4.27 (dd, J=15 Hz and J=7 Hz, 1H), 4.42 (dd, J=15 Hz and J=4 Hz, 1H), 5.45 (d, J=5 Hz, 1H), 6.60 (d, J=3 Hz, 1H), 7.04 (d, J=9 Hz, 2H), 7.30 (d, J=8 Hz, 1H), 7.40 (d, J=8 Hz, 2H), 7.45 (d, J=8 Hz, 2H), 7.58 (d, J=3 Hz, 1H), 7.59 (d, J=7 Hz, 1H), 7.62 (m, 2H), 7.72 (d, J=8 Hz, 1H), 8.35 (s, 1H)

B. 1-[3-(Biphenyl-4-yloxy)-2-hydroxypropyl]indole-5-carbamide

The preparation is based on 1-[3-(biphenyl-4-yloxy)-2-hydroxypropyl]indole-5-carbonitrile in analogy to the synthesis of step C of Example 26. The product is obtained as a solid.

Mp.: 155° C.

$C_{24}H_{22}N_2O_3$ (386.4)

$^1$H-NMR (DMSO-d$_6$): δ (ppm)=3.88-3.92 (m, 2H), 4.19 (s, broad, 1H), 4.27 (dd, J=14 Hz and J=7 Hz, 1H), 4.41 (dd, J=14 Hz and J=4 Hz, 1H), 5.48 (s, broad, 1H), 6.51 (d, J=3 Hz, 1H), 7.02 (d, J=9 Hz, 2H), 7.10 (s, broad, 1H), 7.28-7.32 (m, 1H), 7.36-7.43 (m, 3H), 7.48-7.63 (m, 6H), 7.83 (s, broad, 1H), 8.17 (s, 1H)

C. 1-[3-(Biphenyl-4-yloxy)-2-oxopropyl]indole-5-carbamide

The preparation is based on 1-[3-(biphenyl-4-yloxy)-2-hydroxypropyl]indole-5-carbamide in analogy to the synthesis of step D of Example 26. The product is obtained as a solid.

Mp.: 120° C.

$C_{24}H_{20}N_2O_3$ (384.4)

$^1$H-NMR (DMSO-d$_6$): δ (ppm)=5.09 (s, 2H), 5.21 (s, 2H), 6.57 (d, J=3 Hz, 1H), 7.09 (d, J=9 Hz, 2H), 7.11 (s, broad, 1H), 7.28-7.33 (m, 1H), 7.35 (d, J=3 Hz, 1H), 7.38-7.45 (m, 3H), 7.57-7.70 (m, 4H), 7.85 (s, broad, 1H), 8.17 (s, 1H)

EXAMPLE 28

1-[3-(Biphenyl-3-yloxy)-2-oxopropyl]indole-5-carbamide

A. 1-[3-(Biphenyl-3-yloxy)-2-hydroxypropyl]indole-5-carbonitrile

The preparation is based on 3-phenyl phenol and 1-oxiranylmethylindole-5-carbonitrile in analogy to the synthesis of step A of Example 27. The product accrues as a solid.

Mp.: 120° C.

$C_{24}H_{20}N_2O_2$ (368.4)

$^1$H-NMR (DMSO-d$_6$): δ (ppm)=3.95 (m, 2H), 4.19 (m, 1H), 4.32 (dd, J=14 Hz and J=7 Hz, 1H), 4.48 (dd, J=14 Hz and J=4 Hz, 1H), 5.49 (d, J=5 Hz, 1H), 6.61 (d, J=3 Hz, 1H), 6.94 (m, 1H), 7.18 (d, J=2 Hz, 1H), 7.24 (d, J=8 Hz, 1H), 7.37 (m, 2H), 7.42-7.51 (m, 3H), 7.58 (d, J=3 Hz, 1H), 7.65 (m, 2H), 7.72 (d, J=8 Hz, 1H), 8.09 (s, 1H)

B. 1-[3-(Biphenyl-3-yloxy)-2-hydroxypropyl]indole-5-carbamide

The preparation is based on 1-[3-(biphenyl-3-yloxy)-2-hydroxypropyl]indole-5-carbonitrile in analogy to the synthesis of step C of Example 26. The product is obtained as a solid.

Mp.: 162° C.

$C_{24}H_{22}N_2O_3$ (386.4)

$^1$H-NMR (DMSO-d$_6$): δ (ppm)=3.95 (m, 2H), 4.20 (s, broad, 1H), 4.29 (dd, J=15 Hz and J=7 Hz, 1H), 4.42 (dd, J=15 Hz and J=4 Hz, 1H), 5.43 (s, broad, 1H), 6.45 (d, J=3 Hz, 1H), 6.97 (dd, J=8 Hz and J=2 Hz, 1H), 7.17 (s, broad, 1H), 7.18 (d, J=2 Hz, 1H), 7.22 (d, J=8 Hz, 1H), 7.31-7.39 (m, 2H), 7.41-7.51 (m, 3H), 7.60-7.69 (m, 3H), 7.84 (s, broad, 1H), 8.12 (s, 1H)

C. 1-[3-(Biphenyl-3-yloxy)-2-oxopropyl]indole-5-carbamide

The preparation is based on 1-[3-(biphenyl-3-yloxy)-2-hydroxypropyl]indole-5-carbamide in analogy to the synthesis of step D of Example 26. The chromatographic purification is initially carried out on silica gel using the flow agent hexane/ethyl acetate 3:7 and then on an RP-HPLC column (cromasil) using the flow agent acetonitrile/water/formic acid (70:30:0.02). The product accrues as a solid.

$C_{24}H_{20}N_2O_3$ (384.4)

$^1$H-NMR (DMSO-$d_6$): δ (ppm)=5.18 (s, 2H), 5.44 (s, 2H), 6.58 (d, J=3 Hz, 1H), 6.98 (dd, J=8 Hz and J=3 Hz, 1H), 7.18 (s, broad, 1H), 7.20-7.25 (m, 2H), 7.25-7.45 (m, 6H), 7.60-7.71 (m, 3H), 7.83 (s, broad, 1H), 8.18 (s, 1H)

EXAMPLE 29

1-[3-(Biphenyl-2-yloxy)-2-oxopropyl]indole-5-carbamide

A. 1-[3-(Biphenyl-2-yloxy)-2-hydroxypropyl]indole-5-carbonitrile

The preparation is based on 2-phenyl phenol and 1-oxiranylmethylindole-5-carbonitrile in analogy to the synthesis of step A of Example 27. The product accrues as a solid.

Mp.: 117° C.

$C_{24}H_{20}N_2O_2$ (368.4)

$^1$H-NMR (DMSO-$d_6$): δ (ppm)=3.84 (dd, J=10 Hz and J=6 Hz, 1H), 3.94 (dd, J=10 Hz and J=4 Hz, 1H), 4.01-4.08 (m, 1H), 4.09-4.13 (m, 1H), 4.29-4.33 (m, 1H), 5.41 (d, J=5 Hz, 1H), 6.57 (d, J=3 Hz, 1H), 7.01-7.11 (m, 2H), 7.21-7.39 (m, 6H), 7.43-7.51 (m, 2H), 7.61 (d, J=7 Hz, 1H), 8.03 (s, 1H)

B. 1-[3-(Biphenyl-2-yloxy)-2-hydroxypropyl]indole-5-carbamide

The preparation is based on 1-[3-(biphenyl-2-yloxy)-2-hydroxypropyl]indole-5-carbonitrile in analogy to the synthesis of step C of Example 26. The product is obtained as a solid.

Mp.: 150° C.

$C_{24}H_{22}N_2O_3$ (386.4)

$^1$H-NMR (DMSO-$d_6$): δ (ppm)=3.85 (dd, J=9 Hz and J=6 Hz, 1H), 3.92 (dd, J=9 Hz and J=4 Hz, 1H), 4.00-4.10 (m, 2H), 4.20-4.30 (m, 1H), 5.38 (d, J=4 Hz, 1H), 6.45 (d, J=3 Hz, 1H), 6.98-7.12 (m, 4H), 7.23 (d, J=3 Hz, 1H), 7.25-7.50 (m, 5H), 7.52-7.61 (m, 3H), 7.81 (s, broad, 1H), 8.11 (s, 1H)

C. 1-[3-(Biphenyl-2-yloxy)-2-oxopropyl]indole-5-carbamide

The preparation is based on 1-[3-(biphenyl-2-yloxy)-2-hydroxypropyl]indole-5-carbamide in analogy to the synthesis of step D of Example 26. The product accrues as a solid.

$C_{24}H_{20}N_2O_3$ (384.4)

$^1$H-NMR (DMSO-$d_6$): δ (ppm)=5.04 (s, 2H), 5.32 (s, 2H), 6.52 (d, J=3 Hz, 1H), 7.01-7.83 (m, 13H), 7.91 (s, broad, 1H), 8.18 (d, J=1 Hz, 1H)

EXAMPLE 30

1-[3-(1-Heptylindol-5-yloxy)-2-oxopropyl]indole-5-carbamide

A. 5-Benzyloxy-1-heptylindole 0.22 g (4.45 mmol) pulverized, 88% potassium hydroxide, 0.5 g (2.24 mmol) 5-benzyloxyindole and 0.07 g (0.22 mmol) tetrabutylammoniumbromide are weighed out in the given order and mixed with 1.41 ml (8.96 mmol) 1-bromoheptane with vigorous stirring. The mixture is stirred at room temperature overnight. Having added 30 ml water, three extractions using diethyl ether are carried out. The organic phase is washed three times with saturated NaCl solution, dried on sodium sulfate and the solvent is removed in vacuo. The residue is purified on silica gel by means of column chromatography (flow agent: hexane/ethyl acetate 95:5). The product accrues as an oil.

Yield: 530 mg (0.16 mmol), 74%

$^1$H-NMR (CDCl$_3$): δ (ppm)=0.80 (t, J=7 Hz, 3H), 1.13-1.27 (m, 8H), 1.75 (quin, J=7 Hz, 2H), 4.00 (t, J=7 Hz, 2H), 5.05 (m, 2H), 6.31 (d, J=3 Hz, 1H), 6.87 (dd, J=9 Hz and J=3 Hz, 1H), 6.98 (d, J=3 Hz, 1H), 7.08 (d, J=3 Hz, 1H), 7.16 (d, J=9 Hz, 1H), 7.24 (t, J=7 Hz, 1H), 7.31 (m, 2H), 7.41 (d, J=7 Hz, 2H)

B. 1-Heptylindol-5-ol 0.5 g (1.55 mmol) 5-benzyloxy-1-heptylindole is dissolved in a Schlenk flask in 10 ml methanol and 4 ml dichloromethane. 0.06 g Pd (10%)/C is added and the mixture is rinsed with nitrogen for 15 minutes. Thereafter, a balloon filled with hydrogen is placed on the Schlenk piston and hydrogenation is carried out at room temperature for 12 h. The batch is filtrated on a frit and the solvent is removed in vacuo. The residue is purified on silica gel by means of column chromatography (flow agent: hexane/ethyl acetate 9:1). The product accrues as an oil.

Yield: 0.33 g (1.43 mmol); 90%

$C_{24}H_{20}N_2O_3$ (384.4)

$^1$H-NMR (DMSO-$d_6$): δ (ppm)=0.82 (t, J=7 Hz, 3H), 1.21 (m, 8H), 1.72 (quin, J=7 Hz, 2H), 4.05 (t, J=7 Hz, 2H), 6.18 (d, J=3 Hz, 1H), 6.61 (dd, J=9 Hz and J=2 Hz, 1H), 6.82 (d, J=2 Hz, 1H), 7.20 (m, 2H), 8.63 (s, 1H).

C. 1-[3-(1-Heptylindol-5-yloxy)-2-hydroxypropyl]indole-5-carbonitrile

The preparation is based on 1-heptylindol-5-ol and 1-oxiranylmethylindole-5-carbonitrile in analogy to the synthesis of step B of Example 26. The chromatographic purification on silica gel is carried out using the flow agent hexane/ethyl acetate 4:1. The product accrues as an oil.

$C_{27}H_{31}N_3O_2$ (429.6)

$^1$H-NMR (DMSO-$d_6$): δ (ppm)=0.83 (t, J=7 Hz, 3H), 1.13-1.28 (m, 8H), 1.71 (quin, J=7 Hz, 2H), 3.81-3.91 (m, 1H), 4.02 (m, 1H), 4.08 (t, J=7 Hz, 2H), 4.15 (s, broad, 1H), 4.31 (dd, J=14 Hz and J=7 Hz, 1H), 4.46 (dd, J=14 Hz and J=4 Hz, 1H), 5.41 (s, broad, 1H), 6.28 (d, J=3 Hz, 1H), 6.58 (d, J=3 Hz, 1H), 6.80 (dd, J=9 Hz and J=2 Hz, 1H), 6.95 (d, J=2 Hz, 1H), 7.28 (d, J=3 Hz, 1H), 7.34 (d, J=9 Hz, 1H), 7.42 (dd, J=9 Hz and J=2 Hz, 1H), 7.44 (d, J=3 Hz, 1H), 7.68 (d, J=9 Hz, 1H), 8.06 (d, J=2 Hz, 1H)

D. 1-[3-(1-Heptylindol-5-yloxy)-2-hydroxypropyl]indole-5-carbamide

The preparation is based on 1-[3-(1-heptylindol-5-yloxy)-2-hydroxypropyl]indole-5-carbonitrile in analogy to the synthesis of step C of Example 26. The product accrues as a solid.

Mp.: 114° C.

$C_{27}H_{33}N_3O_3$ (447.6)

$^1$H-NMR (DMSO-d$_6$): δ (ppm)=0.83 (t, J=7 Hz, 3H), 1.13-1.28 (m, 8H), 1.71 (quin, J=7 Hz, 2H), 3.81-3.91 (m, 1H), 4.02 (q, J=7 Hz, 1H), 4.08 (t, J=7 Hz, 2H), 4.15 (m, 1H), 4.31 (dd, J=14 Hz and J=7 Hz, 1H), 4.46 (dd, J=14 Hz and J=4 Hz, 1H), 5.40 (d, J=5 Hz, 1H), 6.28 (d, J=3 Hz, 1H), 6.48 (d, J=3 Hz, 1H), 6.80 (dd, J=9 Hz and J=2 Hz, 1H), 6.95 (d, J=2 Hz, 1H), 7.08 (s, broad, 1H), 7.28 (d, J=3 Hz, 1H), 7.34 (d, J=9 Hz, 1H), 7.42 (dd, J=9 Hz and J=2 Hz, 1H), 7.44 (d, J=3 Hz, 1H), 7.68 (d, J=9 Hz, 1H), 7.81 (s, broad, 1H), 8.12 (d, J=2 Hz, 1H)

E. 1-[3-(1-Heptylindol-5-yloxy)-2-oxopropyl]indole-5-carbamide

The preparation is based on 1-[3-(1-heptylindol-5-yloxy)-2-hydroxypropyl]indole-5-carbamide in analogy to the synthesis of step C of Example 9. Deviating therefrom, the reaction time is 20 h. The product is extracted from the reaction batch by means of ethyl acetate. The chromatographic purification on silica gel is made using the flow agent ethyl acetate. Following recrystallization from hexane/ethyl acetate, the product accrues as a solid.

Mp.: 171° C.

$C_{27}H_{31}N_3O_3$ (445.6)

$^1$H-NMR (DMSO-d$_6$): δ (ppm)=0.83 (t, J=7 Hz, 3H), 1.13-1.28 (m, 8H), 1.71 (quin, J=7 Hz, 2H), 4.08 (t, J=7 Hz, 2H), 4.97 (s, 2H), 5.42 (s, 2H), 6.28 (d, J=3 Hz, 1H), 6.48 (d, J=3 Hz, 1H), 6.80 (dd, J=9 Hz and J=2 Hz, 1H), 6.95 (d, J=2 Hz, 1H), 7.12 (s, broad, 1H), 7.28 (d, J=3 Hz, 1H), 7.34 (d, J=9 Hz, 1H), 7.42 (dd, J=9 Hz and J=0 2 Hz, 1H), 7.44 (d, J=3 Hz, 1H), 7.68 (d, J=9 Hz, 1H), 7.82 (s, broad, 1H), 8.12 (d, J=2 Hz, 1H)

EXAMPLE 31

Pharmacological Test

The effectiveness of the compounds according to the invention can be determined by the inhibition of cytosolic phospholipase $A_2$. The test method used was described earlier (Lehr M. et al., *Arch. Pharm. Pharm. Med. Chem.* 2000, 333, 312-314). Here, the arachidonic acid formed by cytosolic phospholipase $A_2$ in intact human platelets following stimulation using calcium ionophor A23187 is detected in the presence and absence of test substances.

The compounds of Examples 2, 5, 6, 7, 8 and 9 according to the invention were tested by means of this test system. At a concentration of 10 μM they inhibited the activity of cytosolic phospholipase $A_2$ by 40% to 95%, which proves their effectiveness.

The invention claimed is:

1. A compound of formula I

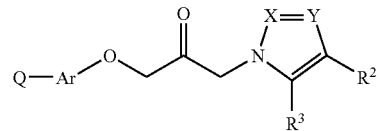

wherein

Q represents $R^1$, $OR^1$, $SR^1$, $SOR^1$, $SO_2R^1$, $NR^9R^1$ or a straight-chain $C_{1-31}$ alkyl or $C_{2-31}$ alkenyl or alkinyl group which is optionally interrupted by 1 or 2 groups, independently selected from O, S, SO, $SO_2$, $NR^9$ and aryl which are optionally substituted with 1 or 2 substituents $R^4$, and which are optionally substituted with 1-4 $C_{1-6}$ alkyl groups and/or 1 or 2 aryl groups, wherein the aryl groups is optionally substituted with 1 or 2 substituents $R^4$;

Ar represents an aryl group selected from the group consisting of a phenyl, naphthyl, biphenyl, and 5-membered heterocylic ring and 6-membered heterocyclic ring, said aryl group containing 1 to 3 atoms selected from O, N, or S and optionally annellated using a benzene ring and further which is optionally substituted with 1 or 2 substituents $R^4$;

X represents N or $CR^5$;

Y represents N or $CR^6$;

$R^1$ represents H or an aryl group which is optionally substituted with 1 or 2 substituents $R^4$;

$R^2$ and $R^3$ a) independently stand for H, $C_{1-6}$ alkyl, $C_{2-6}$ alkenyl, $C_{2-6}$ alkynyl or $R^7$—W, or b) together with the carbon atoms to which they are bound, form a 5- or 6-membered aromatic or heteroaromatic ring which is optionally substituted with 1 or 2 substituents $R^4$;

$R^4$ represents $C_{1-6}$ alkyl, halogen, $CF_3$, CN, $NO_2$, $OR^9$, $S(O)_oR^9$, $COR^9$, $COOR^9$, $CONR^9R^{10}$, $SO_3R^9$, $SO_2NR^9R^{10}$, tetrazolyl or $R^7$—W $R^5$ represents H or $R^4$;

$R^6$ represents H, $C_{1-6}$ alkyl, halogen, $CF_3$, CN, $NO_2$, $OR^9$, $S(O)_oR^9$, $COR^9$, $COOR^9$, $CONR^9R^{10}$, $SO_3R^9$, $SO_2NR^9R^{10}$, tetrazolyl or $R^8$—W;

$R^7$ represents $C_{1-6}$ alkyl, $C_{2-6}$ alkenyl or $C_{2-6}$ alkynyl;

$R^8$ represents $C_{2-6}$ alkyl, $C_{2-6}$ alkenyl or $C_{2-6}$ alkynyl;

$R^9$ represents H, $C_{1-6}$ alkyl or aryl;

$R^{10}$ represents H or $C_{1-6}$ alkyl;

W represents COOH, $SO_3H$ or tetrazolyl; and o represents 0, 1 or 2;

and the pharmaceutically compatible salts and esters thereof.

2. The compound according to claim 1, wherein Q represents $R^1$—$(CHR^{11})_p$—A—$Z^2$—B—$Z^1$— wherein

A represents a bond or a straight-chain $C_{1-m}$ alkyl residue or $C_{2-m}$ alkenyl or alkinyl group;

B represents a bond or a straight chain $C_{1-n}$ alkyl residue or $C_{2-n}$ alkenyl or alkynyl group;

$R^{11}$ represents H or an aryl group which is optionally substituted with 1 or 2 substituents $R^4$;

$Z^1$ and $Z^2$ independently represent a bond, O, S, SO, $SO_2$, $NR^9$, $CR^9R^{10}$ or an aryl group, wherein the aryl group is optionally substituted with 1 or 2 substituents $R^4$;

$R^1$, $R^4$, $R^9$ and $R^{10}$ are as defined in claim 1;

p represents 0 or 1;

m represents an integer from 0 to 12; and n represents an integer from 0 to 16.

3. The compound according to claim 2, wherein m+n≦17.

4. The compound according to claim 2, wherein Q is selected from the group consisting of:
R¹—B—Z¹—
R¹—CHR¹¹—B—Z¹—
R¹—A—Z²—B—Z¹— and
R¹—CHR¹¹—A—Z²—B—Z¹—,
Wherein A, B, R¹, R¹¹, Z¹, Z², n and m are as defined in claim 2.

5. The compound according to claim 4, wherein Q represents phenyl or $C_{5-12}$ alkyl or alkoxy.

6. The compound according to claim 1, wherein Ar represents a phenyl or indolyl group.

7. The compound according to claim 1, wherein R² and R³
a) independently represent H, $C_{1-6}$ alkyl, $C_{2-6}$ alkenyl, $C_{2-6}$ alkynyl or R⁷—W or
b) together with the carbon atoms to which they are bound form a benzo ring or a 6-membered aromatic heterocyclic ring having 1-3 nitrogen atoms, wherein the benzo ring or the heterocyclic ring is optionally substituted with 1 or 2 substituents R⁴, and R⁴ is defined as in claim 1.

8. The compound according to claim 7, wherein R² and R³ represent H or together with the carbon atoms to which they are bound form a benzo ring which is optionally substituted with a substituent R⁴.

9. The compound according to claim 1, wherein X═CR⁵ and Y═CR⁶ or X═N and Y═CR⁶, wherein R⁵ and R⁶ are as defined in claim 1.

10. A pharmaceutical preparation comprising a compound of general formula I according to claim 1 or a pharmaceutically compatible salt or ester thereof.

11. A method of producing a compound of formula I according to claim 1, wherein a compound of formula II

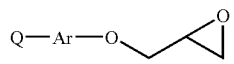

or a compound of formula III

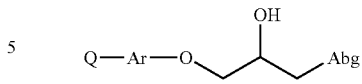

is reacted with a compound of formula IV

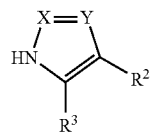

and the alcohol formed is oxidized into the desired ketone, wherein Q, Ar, X, Y, R² and R³ are as defined in claim 1 and Abg represents a leaving group.

12. The compound according to claim 3, wherein Q is selected from
R¹—B—Z¹—
R¹—CHR¹¹—B—Z¹—
R¹—A—Z²—B—Z¹— and
R¹—CHR¹¹—A—Z²—B—Z¹—.

13. The compound according to claim 4, wherein Q represents phenyl or $C_{5-12}$ alkyl or alkoxy.

14. The compound according to claim 5, wherein Q represents $C_{7-10}$ alkyl or alkoxy.

15. The compound according to claim 8, wherein substituent R⁴ is selected from the group consisting of COOH, CH₃, Cl, OCH₃, CN, CHO, COOCH₃ and CONH₂.

16. The compound according to claim 9, wherein R⁵ and R⁶ are independently selected from the group consisting of H, COOH, t-butyl, Cl, CHO, COCH₃ and COOCH₃.

17. The compound according to claim 13, wherein Q represents $C_{7-10}$ alkyl or alkoxy.

18. The method according to claim 11, wherein the leaving group is a halogen.

* * * * *